United States Patent [19]

Pioch

[11] Patent Number: 4,760,075
[45] Date of Patent: * Jul. 26, 1988

[54] N-THIAZOLYLMETHYLTHIOALKYL-N-ALKYL-AMIDINES AND RELATED COMPOUNDS

[75] Inventor: Richard P. Pioch, Indianpolis, Ind.

[73] Assignee: Eli Lilly and Company, Indianapolis, Ind.

[*] Notice: The portion of the term of this patent subsequent to May 3, 2000 has been disclaimed.

[21] Appl. No.: 814,274

[22] Filed: Dec. 23, 1985

Related U.S. Application Data

[63] Continuation of Ser. No. 734,235, May 14, 1985, abandoned, which is a continuation of Ser. No. 486,621, Apr. 20, 1983, abandoned, which is a continuation-in-part of Ser. No. 319,155, Nov. 6, 1981, Pat. No. 4,382,090, which is a continuation-in-part of Ser. No. 193,192, Oct. 2, 1980, Pat. No. 4,375,547.

[51] Int. Cl.$^4$ ............... A61K 31/425; C07D 277/30
[52] U.S. Cl. .................. 514/365; 514/320; 514/926; 514/927; 514/236.8; 544/133; 546/209; 548/203; 548/204; 548/205
[58] Field of Search ............ 514/365, 926, 927; 548/202, 203, 205, 204, 208; 844/133; 546/209; 714/230, 326, 365

[56] References Cited

U.S. PATENT DOCUMENTS

| | | | |
|---|---|---|---|
| 4,001,241 | 1/1977 | Van Hoeven et al. | 548/204 |
| 4,128,658 | 12/1978 | Price et al. | 424/274 |
| 4,165,377 | 8/1979 | Jones et al. | 548/337 |
| 4,173,644 | 11/1979 | Brown et al. | 548/205 |
| 4,200,578 | 4/1980 | Algieri et al. | 548/205 |
| 4,252,819 | 2/1981 | Hirata et al. | 548/205 |
| 4,256,752 | 3/1981 | von Bebenburg et al. | 548/205 |
| 4,374,248 | 2/1983 | Crenshaw et al. | 548/204 |
| 4,382,090 | 5/1983 | Pioch | 548/205 |
| 4,388,319 | 6/1983 | Durant et al. | 548/204 |

OTHER PUBLICATIONS

Streett et al., *Scand. J. Gastroenterol*, 19 (Suppl. 101).
Gilman et al., Proc 1st Medicinal Chemistry Symposium, *Soc. Chem. Ind.* 1981, pp. 58-76.

*Primary Examiner*—Robert Gersil
*Attorney, Agent, or Firm*—Robert A. Conrad; Leroy Whitaker

[57] ABSTRACT

N-alkyl-N'-(2-aminomethyl-4-thiazolylmethylthio)alkyl guanidines, thioureas, ethenediamines and related compounds, $H_2$-receptor antagonists, useful in inhibiting gastric acid secretion in mammals.

24 Claims, No Drawings

N-THIAZOLYLMETHYLTHIOALKYL-N-ALKYL-AMIDINES AND RELATED COMPOUNDS

CROSS-REFERENCE

This application is a continuation of Ser. No. 734,235 filed May 14, 1985 which is a continuation of Ser. No. 486,621 filed on Apr. 20, 1983 both now abandoned which is a continuation-in-part of my copending application Ser. No. 319,155 filed Nov. 6, 1981 now U.S. Pat. No 4,382,090 which was a continuation-in-part of my then copending application 193,192, filed Oct. 2, 1980 now U.S. Pat. No. 4,375,547.

BACKGROUND OF THE INVENTION

Over the past few years, several research groups in, chiefly, England or the United States of America, have synthesized histamine $H_1$ or $H_2$-receptor antagonists. The $H_2$-receptor antagonists are useful in treating peptic ulcers. Broadly speaking, these compounds can be classed as substituted amidines; e.g., acetamidine,

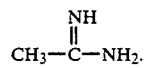

Related compounds include guanidines,

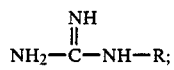

mercaptoamidines or isothioureas,

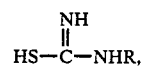

tautomeric with the thioureas

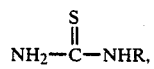

and ethenediamines,

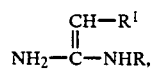

tautomeric with

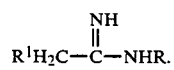

In these new $H_2$-receptor antagonists, the amidine or similar moiety usually occurs at one end of a bridging group; i.e., $-CH_2-Y-(CH_2)_2-$ where Y is S, O, NH or $CH_2$. The other end of the bridging group has usually been an aromatic heterocycle, most frequently imidazole. The heterocyclic ring can be substituted.

The first drug recognized as a powerful $H_2$-receptor antagonist was a thiourea, burimamide—N-methyl-N'-(4-[4(5)-imidazolyl)]butyl)thiourea—having the following formula:

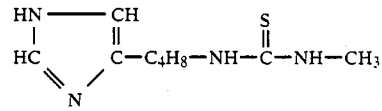

The pharmacological properties of this compound are disclosed in *The Pharmacological Basis of Therapeutics*, Goodman & Gilman 5th Ed. (MacMillan Publishing Co., Inc., New York) page 612. Burimamide was developed by a group of research workers headed by Black and Durant.

A second generation of histamine $H_2$-receptor antagonists comprised compounds developed by Black, Durant and co-workers with a structure more or less similar to that of burimamide, but in which there was a permissible interrupting group—oxygen, sulfur or NH—in the alkyl side chain attached to the hetero ring. The most prominent of this group of compounds has been cimetidine, chemically N-cyano-N'-methyl-N''-[2-([(5-methyl-1H-imidazol-4-yl)methyl]thio)ethyl]guanidine, represented by the formula below:

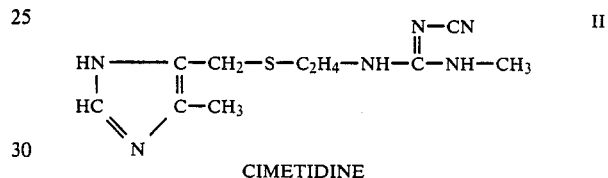

CIMETIDINE

A large number of patents based upon several original filings (Ser. Nos. 230,451; 284,992; 385,027; 481,716; 816,420; 436,285; 542,971; 468,617; 384,993; and 385,027) have issued to Durant et al including, but not limited to, the following U.S. Pat. Nos. 3,950,333; 4,049,672; 4,255,428; 4,154,834; 4,216,318; 4,234,585; 4,022,797; 4,137,237; 4,024,271; 4,070,475; 4,154,844; 3,905,984; 4,027,026; 3,932,427; 4,018,928; 3,950,353; 4,053,473; 4,018,931; 4,069,327; 4,151,288; 4,000,296; 4,083,988; 4,129,657; 4,098,898; 4,166,856; 4,072,748; 3,971,786; 4,060,620; 3,876,647; 3,920,822; 3,897,444; 3,975,530; 4,226,874; 4,228,291; 4,230,865 and 4,221,802.

Other disclosed hetero ring systems in addition to imidazole include pyrazole, pyridine, pyrimidine, pyridazine, thiazole, isothiazole, oxazole, isoxazole, triazole, thiadiazole, benzimidazole and tetrahydroimidazo[1,5-a]pyridine, but the greatest emphasis has continued to be placed on compounds having an imidazole ring system. Groupings which may be present at the terminal end of the alkyl or alkylthioalkyl bridging group include, among others, guanidine, cyanoguanidine, urea, nitroethenediamine and thiourea, plus, more recently, substituted pyrimidones.

Patents referring to thiazole or oxazole ring systems are of particular relevance to this invention. The two basic disclosures by the Durant group are contained in U.S. Pat. Nos. 3,950,333 and 3,950,353, both of which are continuations-in-part of Ser. No. 290,584 which was in turn a continuation-in-part of Ser. No. 230,451. In U.S. Pat. No. 3,950,333, the disclosure relating to thiazoles begins at Example 115, column 37. Thiazoles substituted with a chloro or an alkyl group are described. The thiazole nucleus is then attached at the 2- or 4-position of the thiazole ring to an alkylthioalkyl side chain terminating in an N-cyano-N'-methylguanidine. This disclosure is followed by similar disclosures for isothiazoles, oxazoles and isoxazoles. The disclosure in U.S. Pat. No. 3,950,353 relating to thiazoles begins at Example 110, column 37. Here, substantially the same thiazole nucleus is attached via a bridging group to an N-methylthiourea. A similar disclosure is present for isothiazoles, oxazoles and isoxazoles. U.S. Pat. No. 4,022,797, a division, specifically claims the cyanoguanidine derivatives and U.S. Pat. No. 4,137,234, another division, specifically claims thioureas.

U.S. Pat. No. 4,000,296 discloses and claims a group of N-alkyl or N-arylsulfonyl-N'-alkyl-N''-(heterocyclealkylthioalkyl)guanidines in which the heterocycle can be thiazole, isothiazole, oxazole or isoxazole. Alkyl, alkylaminoalkyl and alkyloxyalkyl bridging groups (connecting the heterocycle to the substituted guanidine group) are also disclosed. Substituted heterocycles belonging to any of the above classes are not disclosed. U.S. Pat. No. 4,166,856, originating with the Durant group, discloses and claims a number of imidazoles and thiazoles carrying the usual alkylthioalkyl-guanidine, -thiourea or -ethenediamine side chain, which side chain is invariably attached at the 2-position of the heterocyclic ring.

Another group of investigators under Yellin has disclosed—see U.S. Pat. Nos. 4,165,377, 4,234,735 and 4,165,378—certain novel thiazoles having a side chain such as those discussed above attached at the 4-position of the thiazole ring; i.e, an alkylthioalkyl-guanidine, -ethenediamine or -thiourea group attached thereto, but also bearing a guanidino group in the 2-position of the thiazole. Alkylene, alkenylene and alkyloxyalkyl bridging groups are also disclosed. A representative compound is 2-guanidino-4-[2-(2-cyano-3-methylguanidino)ethylthiomethyl]thiazole which is said to have greatly increased activity over cimetidine.

A third research group at Allen and Hanburys Ltd. has prepared compounds with a furan ring carrying the standard alkylthioalkyl (or alkyloxyalkyl or alkyl) side chain terminating in a substituted guanidine or ethenediamine group, and also having a dialkylaminoalkyl substituent attached at a second position in the furan ring--see U.S Pat. Nos. 4,128,658 and 4,168,855. Several of the compounds thus produced have a greater $H_2$ activity than cimetidine. The most prominent of these is ranitidine

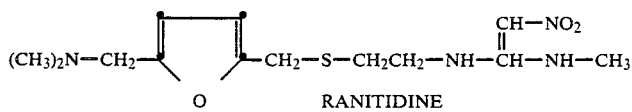

RANITIDINE

Belgian patent Nos. 867,105 and 867,106 disclose the corresponding thiophene and aminoalkylbenzenes. U.S. Pat. No. 4,233,302 from Glaxo also discloses a group of $H_2$-receptor antagonists having a dialkylamino alkyl substituted thiophene or furan as one portion of the molecule.

Finally, a research group at Bristol-Myers has issued several U.S. patents involving different heterocycles. The first of these, U.S. Pat. No. 4,203,909, relates to furans carrying an alkylthioalkyl-guanidine (or thiourea or ethenediamine) side chain in the 2-position, an aminoalkyl side chain in the 5-position and an alkynylamino group as part of the terminal portion of the molecule. One of the compounds, 1-nitro-2-(2-propynylamino)-2-(2-[(5-dimethylaminomethyl-2-furyl)methylthio]ethylamino)ethylene, is said to have 7.45 times the activity of cimetidine in a standard $H_2$-receptor assay. A second patent, U.S. Pat. No. 4,200,578, covers broadly thiazoles substituted with an alkylthioalkyl guanidine (or thiourea or ethenediamine) side chain, and again carrying an obligatory alkynyl group in the terminal portion. Other permissible substituents in the thiazole ring include alkyl, guanidino or amino-alkyl. Despite the broad disclosure, the actual working examples in U.S. Pat. No. 4,200,578 are limited to thiazoles carrying the alkylthioalkylguanidine, etc. side chain in the 2-position of the thiazole ring except for a few compounds in which the side chain is carried in the 4-position, but in which there is a guanidino group in the 2-position. Synthetic Schemes I through VIII of the patent are suitable only for preparing 2-substituted thiazoles. Example 22 discloses thiazoles substituted in the 4-position but these thiazoles either do not carry a second ring substituent or, if there is one, it is a guanidino group.

U.S. Pat. No. 4,200,760 has a similar disclosure of an ethenediamine carrying an alkynylamine group attached by a bridging group to an imidazole ring. Pyridine is the heterocycle in U.S. Pat. No. 4,250,316. However, a recent Bristol-Myers Belgian patent No. 885,089, published 3-4-81, same as U.K. patent No. 2,067,987, discloses a group of $H_2$-receptor antagonists among which are included compounds of the formula

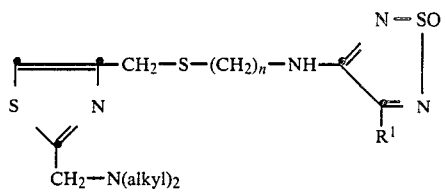

One compound specifically disclosed is prepared from 2-[2-(dimethylaminomethyl)-4-thiazolylmethylthio]ethylamine—See Example 22, part E page 72 et seq.

To summarize, thiazoles in which there is a 4-alkylthioalkyl(or alkyl)-guanidine (or thiourea or ethenediamine) side chain are known wherein the thiazole group can be substituted in the 2- or 5-position with guanidino, methyl, chloro and aminoalkyl. The disclosure relating to thiazoles substituted with an aminoalkyl group at one position in the thiazole ring and, at a second position, a bridging alkylthioalkyl, alkylene, alkenylene or alkyloxyalkyl group terminating in a substituted amidine group, is restricted to amidines carrying an N-alkynyl group as part of the terminal grouping.

SUMMARY OF THE INVENTION

This invention provides compounds of the formula

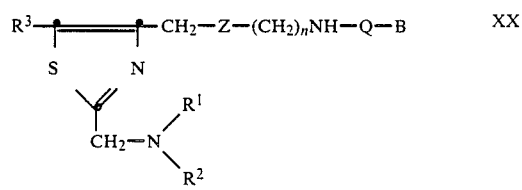

wherein $R^1$ represents hydrogen, methyl, ethyl, benzyl or benzoyl; $R^2$ represents methyl or ethyl; or $R^1$ and $R^2$ taken together with the nitrogen atom to which they are attached, form a pyrrolidine, piperidine or morpholine ring;

$R^3$ is hydrogen or methyl;

Z is O, S or $CH_2$;

n is 2 or 3 when Z is O or S and n is 1, 2 or 3 when Z is $CH_2$;

Q is

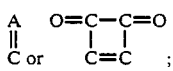

wherein A is N-CN, N-$NO_2$, CH-$NO_2$, S, N-$SO_2$-aryl, N-$SO_2$-methyl, or N-CO-$NH_2$; wherein aryl is tolyl or phenyl; and B is NHR, wherein R is methyl, ethyl, (2-hydroxy)ethyl or cyclopropyl; or B is $YR^4$, wherein Y is oxygen or sulfur and $R^4$ is ($C_1$-$C_3$)alkyl, -$CH_2$-($C_2$-$C_4$)alkenyl or benzyl; provided that when Q is

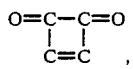

B is NHR or O—($C_1$-$0C_2$)- alkyl; and acid addition salts thereof. Compounds according to XX are particularly effective $H_2$-receptor antagonists, or are useful intermediates in the preparation of such drugs.

Preferred compounds according to XX are those wherein $R^1$ and $R^2$ individually represent methyl or ethyl; or wherein $R^1$ and $R^2$ taken together with the adjacent nitrogen atom represent a piperidino, pyrrolidino or morpholino group; wherein $R^3$ is hydrogen; Q is

A is N-CN, N-$NO_2$, CH-$NO_2$, S, N-$SO_2$-tolyl, N-$SO_2$-phenyl, N-$SO_2$-methyl, or N-CO-$NH_2$, B is NHR; and R is as defined above; and the pharmaceutically-acceptabe, non-toxic acid-addition salts thereof.

A preferred group of intermediate compounds have the same structural characteristics except that B is $YR^4$, Y is S and $R^4$ is ($C_1$-$C_2$)alkyl.

Further preferred features possessed by the $H_2$-receptor antagonists of the invention are those listed below:

(a) Z is S;

(b) n is 2;

(c) $R^3$ is hydrogen;

(d) $R^1$ and $R^2$ are methyl;

(e) A is NCN or $CHNO_2$; and (f) B is methylamino.

In formula XX, when B is $YR^4$, the grouping $YR^4$ in general represents a leaving group such as methylthio, allylthio, or benzylthio. Thus, compounds in which B is $YR^4$ are in general useful as intermediates as are compounds according to XX in which one of $R_1$ or $R^2$ is benzyl, H or benzoyl although such compounds may have modest $H_2$-receptor blocking activity also. Other suitable leaving groups will suggest themselves to those skilled in the art.

The presently preferred compounds of the invention are:

N-methyl-N'-2-(2-dimethylaminomethyl-4-thiazolylmethylthio)ethyl-N"-cyanoguanidine N-methyl-N'-(2-dimethylaminomethyl-4-thiazolylmethylthio)ethyl-2 -nitro-1,1-ethenediamine, and their pharmaceutically-acceptable salts.

Other bases of formula (XX) include:

N-cyclopropyl-N'-2-(2-methylaminomethyl-5-methyl-4-thiazolylmethylthio)ethyl-N"-nitroguanidine N-cyclopropyl-N'-2-[2-(2-diethylamino)methyl-4-thiazolylmethylthio]ethyl-N-4-phenylsulphonylguanidine N-methyl-N'-2-(2-methylaminomethyl-5-methyl-4thiazolylmethylthio)ethylthiourea N-ethyl-N'-2-(2-piperidinomethyl-4-thiazolylmethylthio)ethyl-N"-cyanoguanidine N-(2-hydroxy)ethyl-N'-3-(2-methylaminomethyl-4-thiazolylmethylthio)propyl 2-nitro-1,1-ethenediamine N-(2-hydroxy)ethyl-N'-4-(2-ethylaminomethyl-5-methyl-4-thiazolyl)-1-butyl-N"-cyanoguanidine N-cyclopropyl-N'-2-(4-morpholinomethyl-5-methyl-4-thiazolylmethyloxy)ethylthiourea N-cyclopropyl-N'-3-[2-(1-pyrrolidinomethyl)-4-thiazolylmethyloxy]propylthiourea.

N-cyclopropyl-N'-3-(2-methylaminomethyl-4-thiazolylmethyloxy)propylthiourea

N-methyl-N'-3-(2-diethylaminomethyl-5-methyl-4-thiazolylmethyloxy)propyl-N"-nitroguanidine N-methyl-N'-4-[2-(1-pyrrolidinomethyl)-4-thiazolyl]-1-butyl-N"-aminocarbonylguanidine N-methyl-N'-2-[2-(4-morpholinomethyl)-5-methyl-4-thiazolylmethylthio]ethyl 2-nitro-1,1-ethenediamine and the like.

The pharmaceutically-acceptable acid addition salts of the compounds of this invention include salts derived from non-toxic inorganic acids such as: hydrochloric acid, phosphoric acid, sulfuric acid, hydrobromic acid, hydriodic acid, phosphorous acid and the like, as well as salts derived from non-toxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptaple salts thus include sulfate, pyrosulfate, bisulfate, sulfite, bisulfite, nitrate, phosphate, monohydrogenphosphat, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluene-sulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

Compounds according to XX above have at least one basic center, the aminoalkyl group at C-2 of the thiazole ring but may have a second or third basic salt-forming group. For example, the substituted amidine terminal group can also have nitrogens present which are, depending on the substitution pattern, sufficiently basic to form salts with the stronger nontoxic acids. Thus, di and tri salts of hydrochloric, hydrobromic and similar strong acids are preparable with many of the compounds represented by XX.

The compounds of this invention wherein Z is S or O—in other words, a heteroatom—are conveniently prepared from a (2-aminoalkyl-4-thiazolylmethyl-heteroatom)alkyl amine. The preparation of these starting materials is illustrated in Flow Chart A below using a compound in which the heteroatom is sulfur for exemplary purposes only.

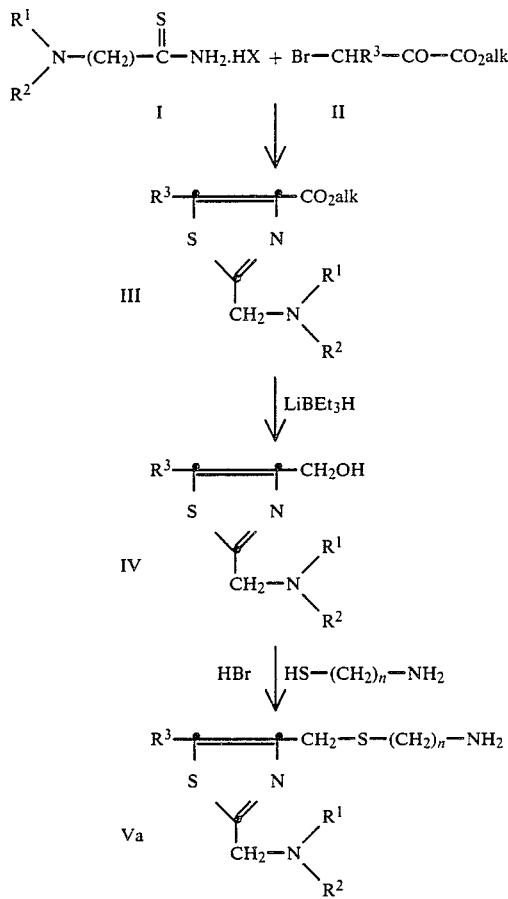

In the above Flow Chart, alk is conveniently methyl or ethyl and $R^1$, $R^2$, $R^3$, and n have the same meaning as hereinabove.

In accordance with the above procedure, an acid addition salt of an aminoalkylthioacetamide (I) is reacted with a beta-bromo-alpha-ketoester (II) such as ethyl bromopyruvate ($R^3=H$) to yield an alkyl (methyl or ethyl) 2-(aminoalkyl)-4-thiazolecarboxylate (III). Reduction of this ester with a suitable hydride reducing agent such as lithium triethylborohydride, lithium aluminumhydride, sodium borohydride, diisobutylaluminumhydride and the like yields the corresponding hydroxymethyl compound (IV). Reaction of the 4-hydroxymethylthiazole with cysteamine or its higher homologue 3-mercaptopropylamine in the presence of acid yields directly a (2-aminomethyl-4-thiazolylmethylthio)alkylamine (Va) optionally substituted with a methyl group in the 5-position of the thiazole ring In the process indicated in Flow Chart A, in going from IV to Va, the hydroxymethyl group can be halogenated as with thionylchloride to yield a 4-chloromethylthiazole and the chlorinated compound in turn reacted with the sodium salt of the particular mercaptoalkylamine. In fact, any standard leaving group (a group labile to nucleophilic displacement) can be employed here in place of chloro in the chloromethyl side chain including for example p-tosyloxy, mesyloxy (methanesulfonyloxy), bromo, iodo and the like.

Alternatively, the 4-chloromethylthiazole hydrochloride (or other suitable acid addition salt) can be fused with a mercaptoalkylamine salt such as a hydrochloride salt to yield the desired primary amine Va.

If it is desired to prepare the oxygen analogue of Va (Z=O), a process utilizing 2-chloroethylamine or 3-chloropropylamine to react with the 4-thiazolemethanol, under basic conditions, can be employed as well as can the analogous Williamson ether process using the sodium salt of the hydroxyalkylamine with a 4-thiazolylmethyl halide.

Several pathways are available for preparing the compounds of this invention. These pathways or synthetic routes may utilize an amine of the generalized formula:

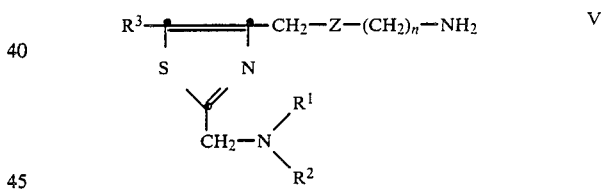

wherein Z is S, O or $CH_2$, as a starting material. These routes are illustrated in Flow Charts B, C and D below. According to Flow Chart B, a starting primary amine, the ultimate product of Flow Chart A (V—Z=S), is reacted with, for example, an N-alkyl or cycloalkyl, 1-methylthio-2-nitroethyleneamine. During the reaction, the elements of methylmercaptan are displaced and the final desired product (VIIa) is an N-2-aminometyl-5-optionally-substituted-4-thiazolylmethylthio) alkyl-N'-alkyl or cycloalkyl, 2-nitro-1,1diaminoethylene(OR2-nitro-1,1-ethenediamine). Similarly, the primary amine (Va) can be reacted with an S-methyl-N-alkyl or cycloalkyl, N'-cyanoisothiourea to form the desired product (VIa)—an N-alkyl or cycloalkyl-N'-2-(2-aminomethyl-5-optionally substituted-4-thiazolylmethylthio)-ethyl-N"-cyanoguanidine. Again, in Flow Chart B, Z is S throughout for convenience only, and the chemistry involved is equally applicable to compounds in which Z is O or $CH_2$.

Flow Chart B

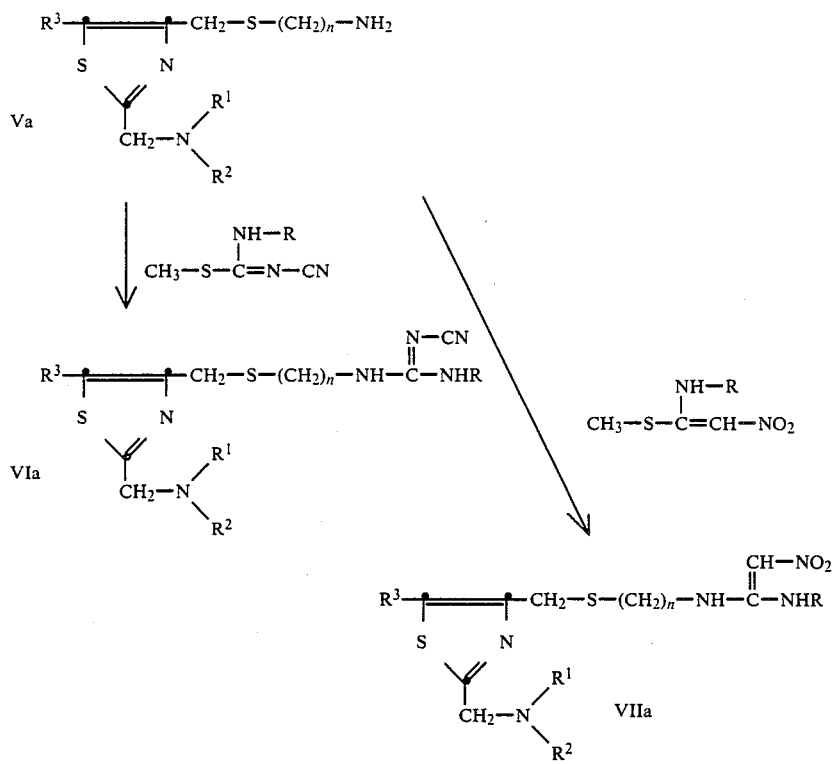

wherein R-R³ and n have the same meaning as hereinabove.

If it is desired to prepare a compound of structure (XX) wherein Q is $$\underset{C}{\overset{A}{\|}}$$

and A is N-SO₂-phenyl, the reagent used to prepare such N''-phenylsulfonylguanidines is dimethyl N-phenylsulfonylimidodithiocarbonate prepared by the general procedure of *Ber.*, 99, 2885 (1966). The methylsulfonylguanidines are produced from a dialkyl N-methylsulfonylimidodithiocarbonate prepared in the same fashion.

Obviously, compounds corresponding to VI and VII in which O replaces S in the bridging group are prepared by substituting a 2-aminoalkyl-4-thiazolylmethoxyalkylamine for Va in Flow Chart B.

Thus, in the general case, compounds of formula (XX) in which B is NHR may be prepared by reacting the amine intermediate of formula V with a compound of the formula L¹QB where L¹ is a leaving group, preferably for ease of preparation, a C₁-C₃ alkylthio, benzylthio or C₂-C₄ alkenylmethylthio group; Q and B being as previously defined.

The reactions of Flow Chart B should be effected in a polar solvent such as water, a C₁-C₄ alkanol or acetonitrile, preferably at a temperature of from 20° to 100° C., most preferably 40° to 50° C.

An example of an alternate method of preparation of the compounds of this invention is illustrated in Flow Chart C. According to this procedure, the same requisite thiazole intermediate (V) is reacted with a 1,1-bis-methylthio-2-nitro ethylene to produce, where Z is S for example, an N-2-(2-aminomethyl-5-optionally-substituted-4-thiazolylmethylthio)ethyl 1-amino-1-methylthio-2-nitro ethyleneamine. Compounds wherein Z is O or CH₂ are prepared similarly.

Flow Chart C

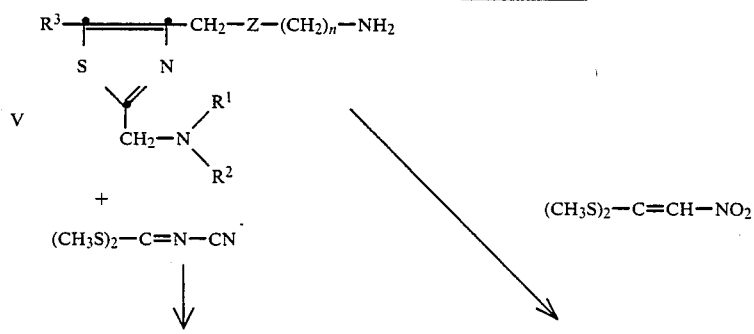

-continued
Flow Chart C

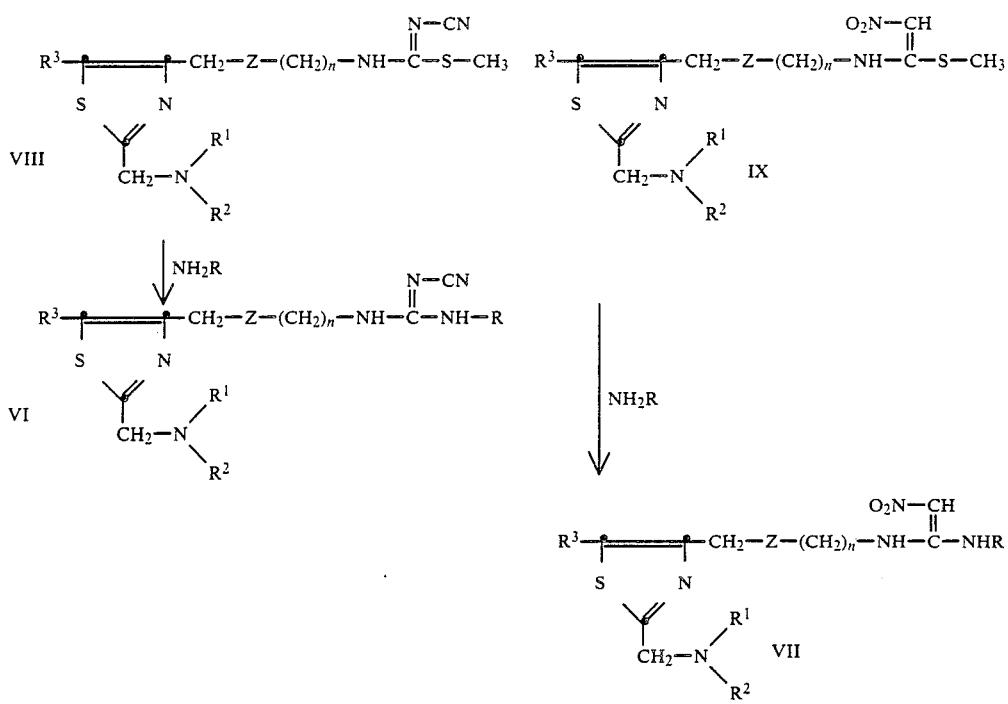

wherein Z, R, $R^1$, $R^2$, $R^3$ and n have the same meaning as hereinabove.

According to Flow Chart C, reaction of the methylmercapto compound VIII or IX with a primary amine $NH_2R$ yields the desired product. Illustratively, dimethylcyanodithioimidocarbonate will react with the thiazolylmethylthioalkylamine or other thiazolyl-side chain-amine (V) to produce, for example, an N-2-(2-aminomethyl-5-optionally-substituted-4-thiazolylmethylthio)ethyl-S-methyl-N'-cyanopseudothiourea (VIII where Z is S). Reaction of this compound with the primary amine $NH_2R$ again yields the desired product VI. Compounds in which A is $CH-NO_2$ as in IX are prepared similarly and react similarly to yield an analogous final product having an ethenediamine terminal group as in VII.

In going from V to IX, 1-methylsulfinyl-1-methylmercapto-2-nitroethylene can be used in place of 1,1-bis-methylmercapto-2-nitroethylene to yield the same intermediate IX since a methylsulfinyl group is displaced preferentially to a methylmercapto group.

Following the above procedure, in certain instances, a reactant such as VIII can be employed in which an $OCH_3$ group replaces the $SCH_3$. This methoxy group is replaceable by the amine $NH_2R$ as is the $S-CH_3$ group illustrated above. For example, a compound of the formula $(CH_3O)_2-C=NCN$ can be employed, or a compound with two different leaving groups such as

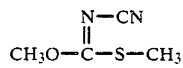

can be employed.

Thus, in the general case, a compound of formula:

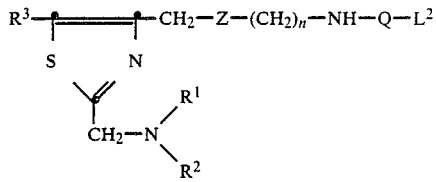

where $L^2$ is a leaving group, preferably a group of formula $YR^4$, can be reacted with an amine of formula $NH_2R$ to yield compounds of formula XX.

The reaction is preferably effected at a temperature from 20° to 100° C. in a polar solvent such as water or a $(C_1-C_4)$alkanol.

A third type of formula XX compound coming within the scope of the above formula are the thioreas wherein A is S. An example of the preparation of such compounds is illustrated in Flow Chart D.

Flow Chart D

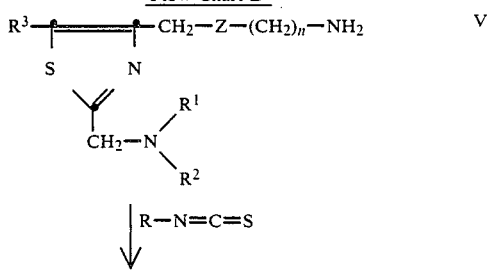

-continued
Flow Chart D

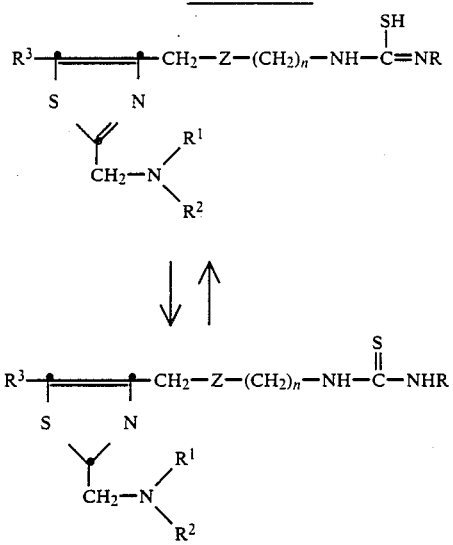

wherein R, R$^1$, R$^2$, R$^3$, Z and n have their previously assigned meanings.

The above procedure can be generalized to use a reagent of the structure R-N=C=A to react with V to produce X. Where A is N-R, the reagent is a carbodiimide; where A is CH-NO$_2$, the reagent is a nitroketeneimine.

According to Flow Chart D, the starting amine, (V), for example a thiazolylmethylthioalkylamine (Z=S), is reacted with a suitably substituted isothiocyanate to yield directly the isothiourea (X) which compound is in equilibrium with the thiourea itself (XI).

In the general case, compounds of formula (XX) in which Q is C=S, may be prepared by reacting a compound of formula (V) with a reagent of the formula

R-N=C=S

The reaction is preferably effected in a polar solvent such as water, a (C$_1$-C$_4$)alkanol or acetonitrile. Preferred reaction temperatures range from 20° to 100° C., most preferably from 40° to 50° C.

Compounds according to XX above in which Q is a 3,4-dioxo-1,2-cyclobutenediyl radical can be prepared in a fashion more or less analogous to the preparation of the corresponding ethenediamines of Flow Chart C, in that the molecule, 1,2-dimethoxy-3,4-dioxocyclobutene, can be reacted with a 2-aminomethyl-4-thiazolylmethylthio(or oxy)alkyl amine to yield a 1-[2-aminomethyl-4-thiazolylmethylthio(or oxy)]alkylamino-2-methoxy-3,4-dioxocyclobutene. This latter compound can then in turn be reacted with an amine, NH$_2$R to yield a compound of formula XX in which B is NHR.

Compounds according to Formula (XX) above wherein A is N-CO-NH$_2$; i.e., having a terminal group of the structure

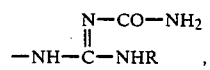

are prepared by hydration of the corresponding cyano compound,

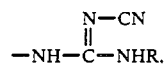

in dilute mineral acid such as, for example, dilute aqueous hydrochloric acid.

Finally, many of the compounds of this invention can be readily prepared via a carbodiimide intermediate as illustrated in Flow Chart E.

Flow Chart E

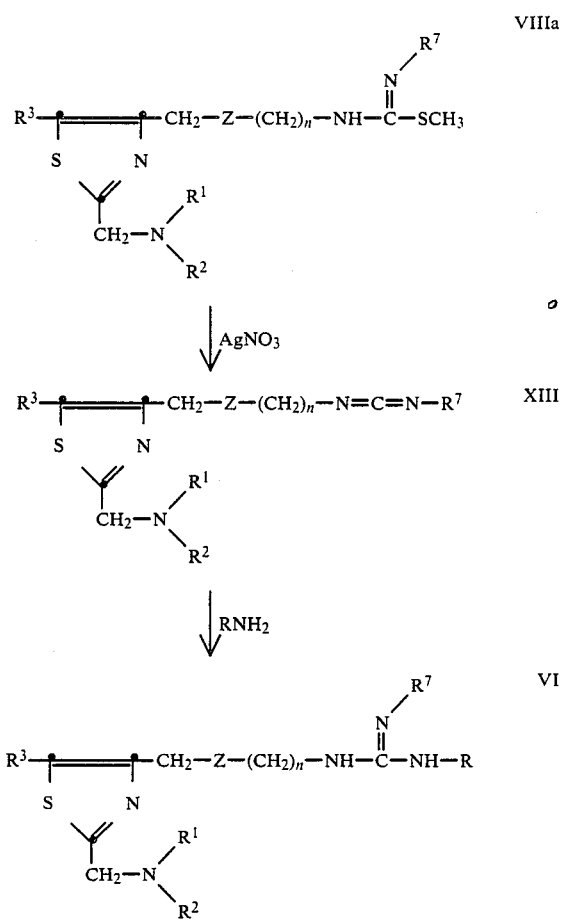

wherein R-R$^4$, Z and n have their previously assigned value and R$^7$ is CN, SO$_2$-aryl or SO$_2$CH$_3$ wherein aryl is phenyl or tolyl.

According to Flow Chart E, an isothiourea VIIIa (prepared by the procedure of Flow Chart C or equivalent procedure) is reacted with silver nitrate to prepare a carbodiimide (XIII), reaction of which with a primary amine, RNH$_2$, yields those compounds of this invention wherein A is NCN etc. (VI).

In the general case compounds of formula XX, where Q is C=A and B is NHR, can be prepared by reacting a compound of formula:

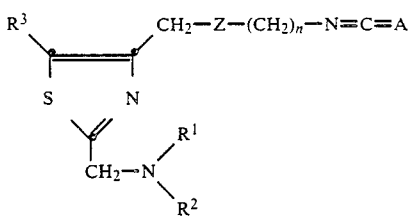

with an amine of formula $RNH_2$.

Compounds of formula XX wherein Z is $CH_2$ and n is 1, 2 or 3, can be prepared by the procedure illustrated in Flow Chart F below.

Flow Chart F

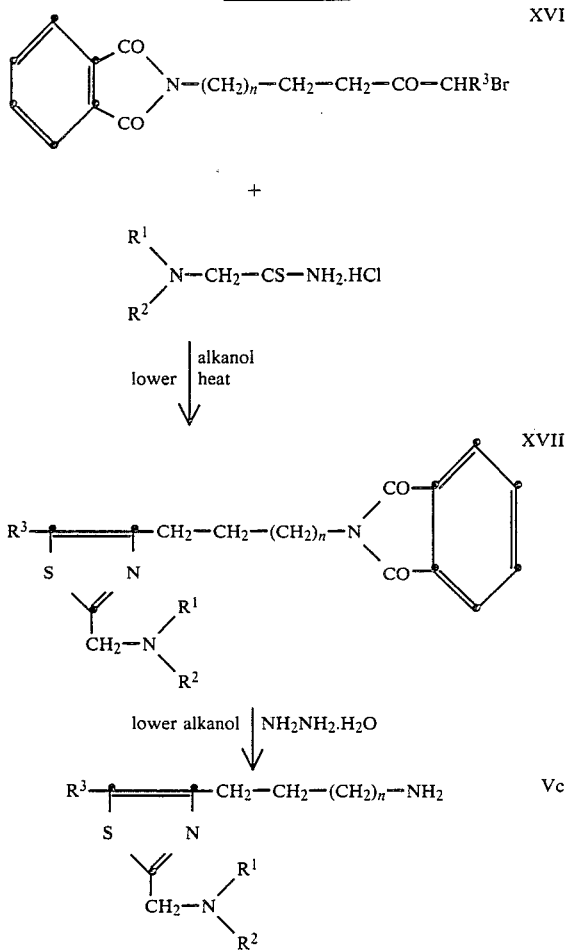

wherein $R^1$, $R^2$, $R^3$, and n have their previously assigned meaning.

According to flow chart F, an omega-(phthalimido)alkyl halomethyl ketone (XVI) is reacted with a dialkylaminothioacetamide hydrochloride to produce a 2-aminomethyl-5-permissibly-substituted-4-omega-(phthalimido)alkylthiazole (XVII). The phthalimido group is removed by hydrazinolysis with hydrazine hydrate to produce the 4-(omega-aminoalkyl)thiazole (Vc). Alkaline hydrolysis with an alkali metal hydroxide followed by treatment with a dilute hydrochloric acid can also be used. This primary amine product (Vc) corresponds to the starting material (Va) produced by flow chart A and can undergo each of the reactions set forth in flow Charts B-E to produce the compounds of this invention wherein Z in formula XX is $CH_2$.

In the above reaction schemes, the aminomethyl group present at position 2 of the thiazole ring has been shown as carrying through each of the reaction steps essentially unchanged from the starting material employed (I in Flow Chart A). At times it is desirable to use certain alternate procedures in those instances where either $R^1$ or $R^2$ is hydrogen For example, where $R^1$ is hydrogen but $R^2$ is methyl or ethyl, it is possible to use a benzyl protecting group through a given reaction scheme to the preparation of the primary amine derivative (Va) at which point the benzyl group can be removed by catalytic hydrogenation to give a secondary amine grouping $NHR^2$. Similarly, an acyl protecting group can be used such as a benzoyl group and this protecting group is removed by reduction to an alcohol during the lithium triethylborohydride reduction step by using excess borohydride.

In Flow Chart G below, a process is illustrated in which a leaving group —$L^3$— is present on the 4-thiazolemethyl moiety and the thiol group is present on, for example, a 1-[2-mercaptoethyl (or 3-mercaptopropyl)amino substituted]-1-alkylamino-2-nitroethenediamine or N-2-mercaptoethyl (or 3-mercaptopropyl)-N'-cyano-N''-alkylguanidine.

Flow Chart G

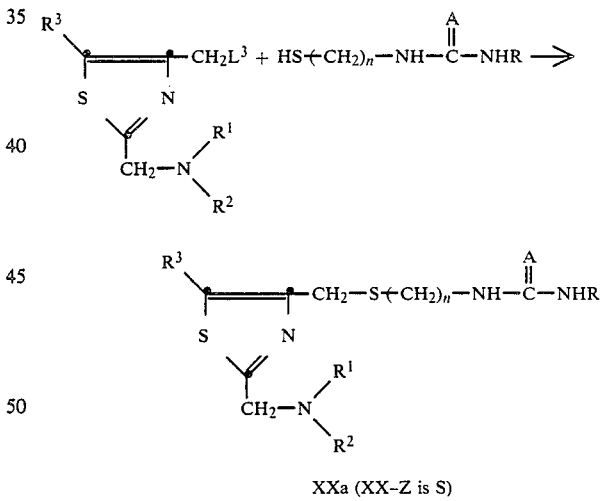

XXa (XX-Z is S)

wherein R—$R^3$ and n have their previous meaning and $L^3$ is a good leaving group such as halo, preferably chloro; sulfonic acid ester such as, for example, tosyloxy or mesyloxy; or OH. The reaction involves, in its simplest aspects, a fusion in the absence of solvent at a temperature in the range 60°–130° C., preferably at 90°–100° C.

In an alternative procedure, the leaving group can be present in the ethenediamine or cyanoguanidine moiety and the thiol group present as such or as a pro-SH group in the dialkylaminomethylthiazole portion, as illustrated below.

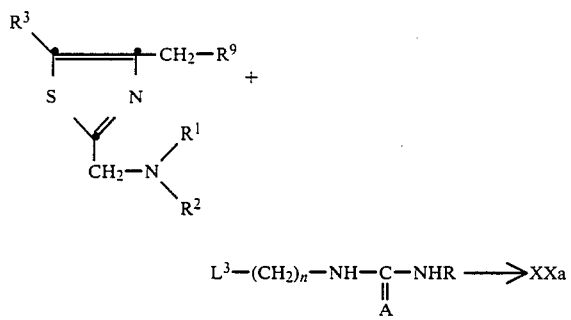

$$L^3-(CH_2)_n-NH-\underset{\underset{A}{\|}}{C}-NHR \longrightarrow XXa$$

where $R^9$ is SH or $$S-\underset{\underset{}{\overset{NH}{\|}}}{C}-NH_2$$

and R, $R^1$, $R^2$, n, A and $L^3$ have the same meaning as hereinabove. $L^3$ is preferably Cl or Br, A is preferably CH—NO$_2$ and $R^9$ is preferably SH.

One starting material for the above synthesis is prepared by reacting the desired 4-chloromethyl-2-aminomethylthiazolehydrochloride or other suitable salt (see discussion following Flow Chart A for preparation) with thiourea. The other starting material where A is CH—NO$_2$ is disclosed in Belgian patent No. 886,997 and where A is N—CN, in U.S. Pat. No. 4,093,621.

In the above structures, the guanidines and ethenediamine terminal groups have been written with structures K and L since it has been believed that these are the most probable structures $$\underset{K}{D-NH-\overset{\overset{N-R^8}{\|}}{C}-NHR} \text{ or } \underset{L}{D-NH-\overset{\overset{CHR^7}{\|}}{C}-NHR} \text{ where D is}$$

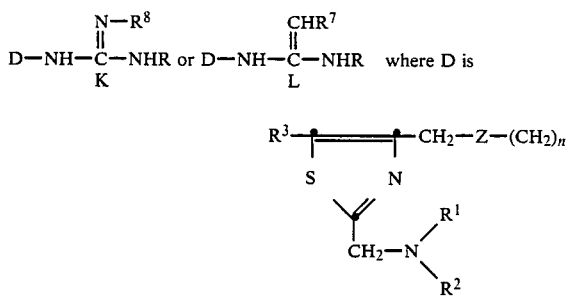

However, as is recognized in the art, K and L represent only one of three possible tautomeric structures, the others being K', K", L' and L".

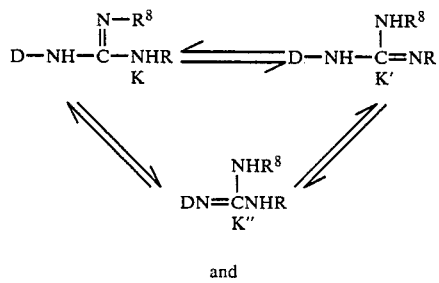

and

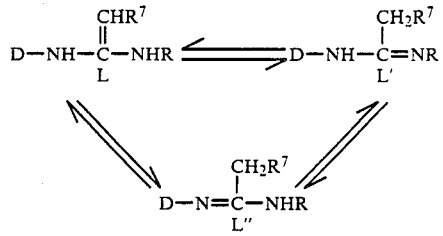

In the above formulas $R^1$, $R^2$, $R^3$, $R^4$, Z, and n have the same meaning previously assigned, $R^7$ is NO$_2$, and $R^8$ is CN, NO$_2$, SO$_2$-aryl, SO$_2$-methyl, or CONH$_2$, wherein aryl is phenyl or tolyl. It is understood in the art that such tautomeric forms exist in equilibrium and, depending on the R, $R^8$, 1 $R^7$ etc. substituent, one form may be more favored in a given substitution pattern. It is also understood that portrayal of a given tautomer in a structure is for convenience only and that all tautomeric forms are included in each such written structure.

This invention is further illustrated by the following examples.

EXAMPLE 1

Preparation of Ethyl 2-Dimethylaminomeithyl-4-thiazolecarboxylate

A reaction mixture was prepared containing 15.5 g. of dimethylaminothioacetamide hydrochloride, 20.5 g. of ethyl bromopyruvate and 100 ml. of ethanol. The reaction mixture was heated to refluxing temperature for about four hours after which time the solvent was removed in vacuo in a rotary evaporator. The residue, containing ethyl 2-dimethylaminomethyl-4-thiazolecarboxylate formed in the above reaction, was dissolved in a mixture of ether and water. The aqueous layer was separated. The ether layer was extracted with an equal volume of water and then discarded. The two aqueous layers were combined and washed with ether. The ether layer was again discarded and the aqueous layer cooled to a temperature in the range of 0°–5° C. Solid potassium carbonate was added until the aqueous layer gave a basic reaction to litmus. An oil separated comprising ethyl 2-dimethylaminomethyl-4-thiazolecarboxylate free base. The oily layer was extracted with ether and the ether extract separated and dried. The ether was removed by evaporation in vacuo. The resulting residue was purified by gradient high pressure liquid chromatography (silica ethyl acetate). Ethyl 2-dimethylaminomethyl-4-thiazolecarboxylate thus obtained had the following physical characteristics:

Analysis Calculated: C, 50.45; H, 6.59; N, 13.07; S, 14.96 Found: C, 50.13; H, 6.39; N, 12.89; S, 15.04.

The nmr spectrum in CDCl$_3$ (TMS internal standard) gave the following signals (δ): 1.43 (triplet, 3H), 2.40 (singlet, 6H), 3.87 (singlet, 2H), 4.47 (quartet, 2H), 8.20 (singlet, 1H).

Following the above procedure, a solution containing 20.4 g. of ethyl bromopyruvate and 20.8 g. of N-methyl-N-benzoyl thioacetamide in 100 ml. of ethanol was heated to refluxing temperature for about 4 hours. The solvent was removed by evaporation in vacuo and the resulting residue dissolved in 65 ml. of 4.5N aqueous hydrochloric acid. The aqueous acidic layer was extracted with ether and the ether extract discarded. 11.5 g. of sodium carbonate were added to the aqueous layer. Ethyl 2-(methylbenzoylaminomethyl)-4- thiazolecarboxylate formed in the above reaction, being insoluble in the solution, separated and was extracted into ether. The ether extract was separated and dried. Evaporation of the ether yielded 20.2 g. of ethyl 2-(methylbenzoylaminomethyl)-4-thiazolecarboxylate melting at about 151.5°–153.5° C. after recrystallization from ethyl acetate.

Analysis Calculated: C, 59.19; H, 5.30; N, 9.20; Found: C, 58.98; H, 5.25; N, 8.90.

The nmr spectrum in CDCl$_3$ (TMS internal standard) gave the following signals ($\delta$): 1.42 (triplet, 3H), 3.07 (singlet, 3H), 4.41 (quartet, 2H), 4.98 (singlet, 2H), 7.40 (apparent singlet, 5H), 8.16 (singlet, 1H).

EXAMPLE 2

Preparation of 2-Dimethylaminomethyl-4-thiazolemethanol

A solution of 12.5 g. of ethyl 2-dimethylaminomethyl-4-thiazolecarboxylate dissolved in about 35 ml. of anhydrous tetrahydrofuran was prepared and then cooled to about 0° C. under a nitrogen atmosphere. About 130 ml. of a 1 molar solution of lithium triethylborohydride in THF was added in dropwise fashion while maintaining the temperature in the range 0°–5° C. The reaction mixture was stirred for about two hours after which time 36 ml. of 6N aqueous hydrochloric acid were added while maintaining the temperature in the range −3° C. to 0° C. The volatile constituents were removed in vacuo on a rotary evaporator. Water was added to the resulting residue and again the volatile constituents were removed. Water was again added to the residue and the aqueous mixture extracted several times with ether. The ether extracts were separated and discarded. The aqueous solution was then chilled and made basic by the addition of solid potassium carbonate. The resulting alkaline aqueous mixture was extracted with ethyl acetate. 2-Dimethylaminomethyl-4-thiazolemethanol, being insoluble in the basic solution, separated and was extracted with several portions of ethyl acetate. The ethyl acetate extracts were combined, and the combined extracts washed with saturated aqueous sodium chloride and then dried. The ethyl acetate was removed by evaporation. The residue consisting of a brown oil weighing about 7.7 g. comprised 2-dimethylaminomethyl-4-thiazolemethanol formed in the above reaction having the following physical characteristics.

Analysis Calculated: C, 48.81; H, 7.02; N, 15.26. Found: C, 48.71; H, 6.77; N, 15.85.

The nmr spectrum in CDCl$_3$ (TMS internal standard) gave the following signals ($\delta$): 2.33 (singlet, 6H), 3.74 (singlet, 2H), 4.32 (singlet, 1H), 4.72 (singlet, 2H), 7.15 (singlet, 1H).

Boiling point = 102° C. at 0.5 torr.

Following the above procedure, 22.5 g. of ethyl N-methyl-N-benzoyl 2-aminomethyl-4-thiazolecarboxylate were dissolved in 125 ml. of dry THF under a nitrogen atmosphere. 320 ml. of a 1M LiEt$_3$BH in THF was added. (Excess borohydride was required over the amount in the above example because of the necessity of reducing both the ethyl ester group to a hydroxymethyl group and of removing the benzoyl group as benzyl alcohol leaving a secondary amine). The reaction mixture was worked up in accordance with the above procedure by decomposition with 6N aqueous hydrochloric acid and water. The residue remaining after the volatile constituents had been removed was a thick oil which was taken up in a little water and 60 ml. of ether.

1 ml. of 12N aqueous hydrochloric acid was added, thus making the aqueous phase strongly acidic. The ether layer was separated and the aqueous layer extracted five more times with equal portions of ether. The ether extracts were discarded. The water layer was separated and the water removed by evaporation in vacuo. The acidic residue was made strongly basic (while being cooled) with 50% aqueous sodium hydroxide (6 grams in 6 ml. of water). 2-Methylaminomethyl-4-thiazolemethanol produced by the above series of reactions was insoluble in the alkaline layer and separated. The compound was taken up in ethyl acetate using a continuous extractor. Removal of the solvent left a tannish oily residue weighing 10.7 grams comprising 2-methylaminomethyl-4-thiazolemethanol. The compound was converted to the dihydrochloride salt by standard laboratory procedures.

Alternatively, a mixture of 2.14 g of ethyl 2-dimethylaminomethyl-4-thiazolecarboxylate and 0.38 g of sodium borohydride in 20 ml. of isopropanol was heated with stirring at reflux temperature for about 14 hours. The reaction mixture was cooled, and 2 ml. of water were added carefully followed by 4 ml. of 5N aqueous hydrochloric acid. The volatile constituents were removed by evaporation. Methanol (10 ml.) was added and the mixture heated to refluxing temperature for about one hour. Methanol was removed by evaporation and the residual solids digested in 10 ml. of isopropanol on the steam bath. The isopropanol solution was separated by decantation and the solids reextracted with 10 ml. of isopropanol. The isopropanol solutions and extracts were combined and the combined solution filtered while hot to remove insoluble material. The filtrate was chilled and a crystalline solid appeared which separated and was recovered by filtration. Recrystallization of the filter cake from isopropanol gave 1.73 g of 2-dimethylaminomethyl-4-thiazolemethanol hydrochloride melting at 153°–154° C.

Analysis: Calculated: C, 40.28; H, 6.28; Cl, 16.99; N, 13.42. Found: C, 40.38; H, 5.04; Cl, 17.24; N, 13.12.

The methanols produced by the process of this example are readily converted to the corresponding thiazolemethyl chlorides according to the following procedure: A suspension was prepared from 1.05 grams of 2-dimethylaminomethyl-4-thiazolemethanol hydrochloride and 15 ml. of chloroform. Thionyl chloride (2.50 g) was added and the resulting mixture was stirred at reflux temperature for about 2.75 hours. Any volatile constituents including excess thionyl chloride were removed by evaporation. The residue was suspended in chloroform and the chloroform removed by evaporation. The residue was then recrystallized from a methanol-ethyl acetate solvent mixture to yield 2-dimethylaminomethyl-4-thiazolylmethylchloride hydrochloride melting at 136°–8° C.

Analysis: Calculated: C, 37.01; H, 5.32; Cl, 31.21; N, 12.33. Found: C, 37.13; H, 5.06; Cl, 31.41; N, 12.36.

EXAMPLE 3

Preparation of 2-(2-Dimethylaminomethyl-4-thiazolylmethylthio)ethylamine

A reaction mixture was prepared from 18.8 g. of 2-dimethylaminomethyl-4-thiazolemethanol, 12.8 g. of 2-aminoethanethiol hydrochloride (cysteamine hydrochloride) and 160 ml. of 48% aqueous hydrobromic acid. The reaction mixture was stirred at about 100° C.

for about 11 hours. The volatile constituents were removed in vacuo on a rotary evaporator. Water was added and the volatile constituents again removed by evaporation. The resulting residue, comprising 2-(2-dimethylaminomethyl-4-thiazolylmethylthio)ethylamine trihydrobromide formed in the above reaction, was dissolved in ethanol. The ethanol was evaporated and the resulting residue again dissolved in ethanol. Evaporation of the ethanol yielded a hygroscopic residue which was recrystallized from a methanol-ethyl acetate solvent mixture. 2-(2-Dimethylaminomethyl-4-thiazolylmethylthio)ethylamine trihydrobromide thus prepared had the following physical characteristics:

Analysis Calculated: C, 22.80; H, 4.25; Br, 50.56; N, 8.86; S, 13.53. Found: C, 23.02; H, 4.31; Br, 50.64; N, 8.80; S, 13.60.

The nmr spectrum in $DMSOd_6$ (TMS internal standard) gave the following signals ($\delta$): 2.55–3.2 (multiplet, 4H), 2.84 (singlet 6H), 3.92 (singlet, 2H), 4.74 (singlet, 2H), 7.2–7.7 (broad, 1H), 7.94 (singlet, 1H), 7.92 (broad, 3H), 10.22 (broad, 1H).

Following the above procedure, 10.1 millimoles of 2-(methylaminomethyl)-4-thiazolemethanol dihydrochloride, 1.15 g. of cysteamine hydrochloride and 15 ml. of 48% aqueous hydrobromic acid were stirred at about 100° C. for about 7.5 hours. Water and hydrobromic acid were removed on a rotary evaporator and the resulting residue comprising 2-(2-methylaminomethyl-4-thiazolylmethylthio)ethylamine trihydrobromide formed in the above reaction was dissolved in water and the water removed by evaporation. The residue was again taken up in water and the water removed by evaporation. The residue was then dissolved in a small volume of water and a solution of 5.5 g. of potassium carbonate in 15 ml. of water was added. The resulting alkaline solution was evaporated to dryness. The resulting residue, comprising the free base of 2-(2-methylaminomethyl-4-thiazolylmethylthio)ethylamine, was slurried with ethanol and the ethanol separated and removed by evaporation. The residue was twice slurried with isopropanol. The residue was next extracted with boiling isopropanol several times and the combined isopropanol extracts combined and filtered. Removal of the isopropanol yielded a yellow oil. The yellow oil was dissolved in chloroform and the chloroform solution filtered. Chloroform was evaporated from the filtrate to yield 1.59 g. of a yellow oil comprising 2-(2-methyl-aminomethyl-4-thiazolylmethylthio)ethylamine. The compound had the following physical characteristics:

The nmr spectrum is $CDCl_3$ (TMS internal standard) gave the following signals ($\delta$): 1.53 (overlapping singlets, 3H), 2.53 (singlet 3H), 2.62 (triplet, 2H), 2.86 (triplet, 2H), 3.81 (singlet, 2H), 4.04 (singlet, 2H), 7.04 (singlet, 1H).

The above primary amine can be prepared by an alternate procedure involving the fusion of a 2-dialkylaminomethyl-4-isothiazolylmethylchloride acid addition salt with an acid addition salt of cysteamine (or homocysteamine). This alternate procedure is illustrated below.

2-Dimethylaminomethyl-4-thiazolylmethylchloride hydrochloride (1.92 g.) and cysteamine hydrochloride (0.96 g.) were intimately mixed and the mixture heated slowly under anhydrous conditions to about 100° C. over a period of one hour. The reaction mixture was then heated in the range 104°–110° C. for a period of 6 hours at which time the reaction was substantially complete as determined by tlc [silica-95:5 ethanol-$NH_4OH$ (0.88 sp. gr.)]. The reaction mixture was cooled and the cooled melt dissolved in a minimal amount of water. The solution was transferred to a rotary evaporator and the water removed. The resulting residue solidified and the solid was recrystallized from a methanol-ethyl acetate solvent mixture. Hygroscopic crystals of 2-(2-dimethylaminomethyl-4-thiazolylmethylthio)ethyl amine trihydrochloride thus produced melted at about 165°–72° C with evolution of HCl.

Analysis Calculated: C, 31.72; H, 5.91; Cl, 31.21; N, 12.33; S, 18.82. Found C, 31.63; H, 6.15; Cl 31.34; N, 12.62; S, 18.63.

EXAMPLE 4

Preparation of N-methyl-N'-2-(2-dimethylaminomethyl-4-thiazolylmethylthio)ethyl-N''-cyanoguanidine A solution was prepared from 3.07 g. of dimethyl cyanodithioimidocarbonate and 35 ml. of ethanol. A second solution containing 4.62 g. of 2-(2-dimethylaminomethyl-4-thiazolylmethylthio)ethylamine in 50 ml. of ethanol was added in dropwise fashion with stirring to the first solution over a period of about 1.5 hours. The resulting reaction mixture was stirred for an additional 20 hours after which time the volatile constituents were removed in a rotary evaporator. Chromatography of the residue over silica by gradient elution using ethyl acetate containing increasing quantities of methanol as the eluant yielded fractions containing methyl N-2-(2-dimethylaminomethyl-4-thiazolylmethylthio)ethyl-N'-cyanocarbamidothioate, formed in the above reaction. These fractions were combined and the solvent removed from the combined fractions in a rotary evaporator. The residue weighed 4.8 g. and, after recrystallization from carbon tetrachloride, melted at about 75°–77° C.

Analysis Calculated: C, 43.74; H, 5.81; N, 21.25; S, 29.19. Found: C, 43.46; H, 5.71; N, 20.98 S, 29.15

2.52 g. Of the above thioester were dissolved in 12 ml. of methanol. 30 ml. of a 35% solution of methylamine (w/w) in ethanol was added with stirring. After five hours, the solvent and excess amine were removed by evaporation on a rotary evaporator. The residue was purified by gradient elution chromatography (silica-ethyl acetate-methanol. Fractions containing N-methyl-N'-2-(2-(dimethylaminomethyl-4-thiazolylmethylthio)ethyl-N''-cyanoguanidine formed in the above reaction were combined to yield 1.86 g. of a glassy residue upon evaporation of the solvent.

Analysis Calculated: C, 46.13; H, 6.45; N, 26.90. Found: C, 46.43; H, 6.39; N, 26.85.

The nmr spectrum in $CDCl_3$ (TMS internal standard) shows the following signals ($\delta$): 2.34 (singlet, 6H); 2.72 (triplet, 2H); 2.84 (doublet, 3H); 3.42 (multiplet, 2H); 3.74 (singlet, 2H); 3.82 (singlet, 2H); 6.08 (multiplet, 1H); 6.22 (multiplet, 1H); 7.10 (singlet, 1H).

Following the above procedure, but substituting ethylamine for methylamine in the reaction with N-2-(2-dimethylaminomethyl-4-thiazolylmethylthio)ethyl-N'-cyanocarbamidothioate, N-ethyl-N'-2-(2-(dimethylaminomethyl-4-thiazolylmethylthio)ethyl-N''-cyanoguanidine was prepared.

Analysis Calculated for $C_{13}H_{22}N_6S_2$: C, 47.82; H, 6.79; N, 25.74; S, 19.64. Found: C, 48.05; H, 7.01; N, 25.51; S, 19.33.

The nmr spectrum in CDCl₃ (TMS internal standard) shows the following peaks (δ): 1.22 (triplet, 3H), 2.34 (singlet, 6H), 2.72 (triplet, 2H), 3.1-3.55 (multiplets unresolved, 4H), 3.74 (singlet, 2H), 3.82 (singlet, 2H), 5.7 (broad, 1H), 6.0 (broad, 1H), 7.08 (singlet 1H).

EXAMPLE 5

Preparation of
N-2-(2-dimethylaminomethyl-4-thiazolylmethylthio)ethyl-N'-methyl 2-nitro-1,1-ethenediamine A quantity of 2-(2-dimethylaminomethyl-4-thiazolylmethylthio)ethylamine trihydrobromide prepared from 50 g. of 2-dimethylaminomethyl-4-thiazolylmethanol by the procedure of Example 3 were dissolved in 150 ml. of water. A solution of 125 g. of potassium carbonate and 150 ml. of water was carefully added thereto. The water was removed by evaporation in vacuo. The resulting alkaline residue was triturated with ethanol and isopropanol and the alkanols removed therefrom by evaporation. The resulting residue was extracted several times with hot isopropanol and the isopropanol extracts were filtered to remove inorganic salts. Evaporation of the solvent from the filtrate yielded a residue which was dissolved in chloroform and filtered. The chloroform was removed from the filtrate on a rotary evaporator. The resulting residue, comprising the free base of 2-(2-dimethylaminomethyl-4-thiazolylmethylthio)ethylamine, was dissolved in 250 ml. of water. This solution was added to a stirred suspension of 40.7 g. of N-methyl-1-methylthio-2-nitroethyleneamine (prepared according to the procedure of Belgian patent No. 859,388) at 50° C. The solution was stirred at the same temperature for about 4 hours after the addition had been completed. Water was then removed by evaporation in vacuo on a rotary evaporator. The resulting residue was dissolved in ethanol and the solvent removed by evaporation. The residue was crystallized from an ethanol-acetonitrile solvent mixture and recrystallized from ethanol-ethyl acetate solvent mixture to yield 49.5 g. of N-methyl-N'-2-(2-dimethylaminomethyl-4-thiazolylmethylthio)ethyl 2-nitro-1,1-ethenediamine melting at about 130°-132° C.

Analysis Calculated: C, 43.48; H, 6.39; N, 21.13 O, 9.65. Found: C, 43.66; H, 6.40; N, 21.14 O, 9.46.

The nmr spectrum in CDCl₃ (TMS internal standard) gave the following signals (δ): 2.24 (singlet, 6H), 2.68 (triplet, 2H), 2.74 (singlet, 3H), 3.34 (multiplet, 2H), 3.70 (singlet, 2H), 4.84 (singlet, 2H), 6.46 (singlet, 1H), 7.16 (broad, 1H), 7.40 (singlet, 1H), 9.96 (broad, 1H).

Following the above procedure, 2-(2-methylaminomethyl-4-thiazolylmethylthio)ethylamine and N-methyl-1-methylthio-2-nitroethyleneamine were reacted in water solution. The reaction was worked up and the product isolated by the above procedure to yield N-methyl-N'-2-(2-methylaminomethyl-4-thiazolylmethylthio)ethyl 2-nitro-1,1-ethenediamine melting at 105°-107° C. after recrystallization from acetonitrile followed by recrystallization from ethanol.

Analysis Calculated: C, 41.62; H, 6.03; N, 22.06 O, 10.08. Found: C, 41.79; H, 6.10; N, 21.80; O, 10.28.

Following the above procedure, 2-(2-dimethylaminomethyl-4-thiazolylmethylthio)ethylamine was caused to react with N-ethyl-1-methylthio-2-nitroethyleneamine to yield N-ethyl-N'-2-(2-dimethylaminomethyl-4-thiazolylmethylthio)ethyl 2-nitro-1,1-ethenediamine melting at about 89°-90° C.

Analysis Calculated for $C_{13}H_{23}N_5O_2S_2$: C, 45.19, H, 6.71; N, 20.27; O, 9.26; Found: C, 45.32; H, 6.70; N, 20.44; O, 9.49.

EXAMPLE 6

Preparation of
N-methyl-N'-2-(2-dimethylaminomethyl-4-thiazolylmethylthio)ethylthiourea A solution was prepared containing 0.80 g. of 2-(2-dimethylaminomethyl-4-thiazolylmethylthio)ethylamine and 0.29 g. of methylisothiocyanate in 10 ml. of ethanol. The solution was stirred at room temperature for about 17 hours after which time the solvent was removed by evaporation in vacuo. The residual gum, comprising N-methyl-N'-2-(2-dimethylaminomethyl-4-thiazolylmethylthio)ethylthiourea formed in the above reaction, was purified by chromatography over silica using a gradient elution technique with ethyl acetate containing increasing quantities of methanol as the eluant. Fractions containing the above compound were combined and the solvent evaporated therefrom in vacuo, leaving as a residue 0.83 g. of a glassy solid.

Analysis Calculated: C, 43.39; H, 6.62; N, 18.40 S, 31.59. Found: C, 43.62; H, 6.49; N, 18.15; S, 31.70.

The nmr spectrum in CDCl₃ (TMS internal standard) gave the following signals (δ): 2.34 (singlet, 6H), 2.80 (triplet, 2H), 3.00 (doublet, 3H), 3.74 (singlet, 2H), 3.82 (singlet, 2H), 3.6-3.9 (multiplet, 2H), 6.9 (broad, 1H), 7.08 (singlet, 1H), 7.2 (broad, 1H).

EXAMPLE 7

Preparation of
N-methyl-N'-2-(2-dimethylaminomethyl-4-thiazolylmethylthio)ethyl-N''-p-tolylsulfonylguanidine A suspension was prepared by adding 1.35 g. of dimethyl p-toluenesulfonylimidodithiocarbonate to 10 ml. of ethanol. While the suspension was being stirred at ambient temperature, a solution of 1.16 g. of 2-(2-dimethylaminomethyl-4-thiazolylmethylthio)ethylamine in 10 ml. of ethanol was added over a 15 minute period. The reaction mixture was stirred for 2.5 hours after the addition had been completed. The solvent was then removed by evaporation in vacuo. The resulting residue was mixed with 20 ml. of a 35% solution (w/w) of ethanolic methylamine. This reaction mixture was stirred for about 15 hours after which time the solvent and other volatile constituents were removed by evaporation in vacuo. The residue was chromatographed over silica using a gradient elution technique employing ethyl acetate containing increasing quantities of methanol as the eluant. Fractions containing N-methyl-N'-2-(2-dimethylaminomethyl-4-thiazolylmethylthio)ethyl-N''-p-tolylsulfonylguanidine formed in the above reaction were combined and the solvent removed therefrom to leave as a residue 1.9 g. of a glass.

Analysis Calculated: C, 48.95; H, 6.16; N, 15.86; 0, 7.25; S, 21.78. Found: C, 49.25; H, 6.27; N, 16.10; O, 7.45; S, 21.62.

The nmr spectrum in CDCl₃ (TMS internal standard) gave the following signals (δ): 2.34 (singlet, 6H), 2.38 (singlet, 3H), 2.62 (triplet, 2H), 2.80 (doublet, 3H), 3.35-3.55 (multiplet, greater than 2H), 3.72 (singlet, 2H), 3.74 (singlet, 2H), 7.06 (singlet, 1H), 7.18 (doublet, 2H), 7.70 (doublet, 2H).

The above procedure was repeated using dimethyl methanesulfonylimidodithiocarbonate as a starting material. N-methyl-N'-2-(2-dimethylaminomethyl-4- thiazolylmethylthio)ethyl-N''-methanesulfonylguanidine was obtained, m.p. 95°–97° C. after recrystallization from ethyl acetate.

Analysis: Calculated: C, 39.43; H, 6.34; O, 8.75; Found: C, 39.71; H, 6.19; O, 8.72.

EXAMPLE 8

Preparation of N-methyl-N'-2-(2-dimethylaminomethyl-4-thiazolylmethylthio)ethyl-N''-nitroguanidine A reaction mixture was prepared containing 1.2 g. of 2-(2-dimethylaminomethyl-4-thiazolylmethylthio)ethylamine, 0.77 g. of S-methyl-N-methyl-N'-nitroisothiourea and 10 ml. of methanol. The reaction mixture was heated under reflux for 4.25 hours, after which time the solvent was removed by evaporation. The partially solid residue was chromatographed over silica using a gradient elution technique employing ethyl acetate containing increasing quantities of methanol as the eluant. Fractions shown by tlc to contain N-methyl-N'-2-(2-dimethylaminomethyl-4-thiazolylmethylthio)ethyl-N''-nitroguanidine formed in the above reaction were pooled and the solvent removed from the pooled fractions. Trituration of the resulting residue with ether yielded a crystalline solid which, upon recrystallization from a methanol-ethyl acetate solvent mixture, yielded 0.83 g. of crystals melting at about 86.5°–88° C.

Analysis Calculated: C, 39.74; H, 6.06; N, 25.28; O, 9.62; S, 19.29. Found: C, 39.92; H, 5.89; N, 25.15; 0, 9.38; S, 19.49.

EXAMPLE 9

Preparation of N-methyl-N'-2-(2-dimethylaminomethyl-5-methyl-4-thiazolylmethylthio)ethyl 2-nitro-1,1-ethenediamine Following the procedure of Example 1, a reaction mixture containing 33.88 g. of ethyl 2-oxo-3-bromobutyrate [prepared by the procedure of Siefert et al., *Helv. Chim. Acta*, 33, 725 (1950)], 21.52 g. of dimethylaminothioacetamide hydrochloride and 100 ml. of anhydrous ethanol was stirred and heated to refluxing temperature for about 2.5 hours. The reaction mixture was allowed to remain at room temperature overnight after which time it was concentrated by evaporation in vacuo. 100 ml. of an ice-water mixture was added to the resulting residue and the aqueous layer extracted with ethyl acetate. The ethyl acetate layer was discarded. The aqueous layer was cooled and then made basic (pH=11) with 2N aqueous sodium hydroxide. The resulting alkaline layer was extracted several times with equal volumes of ethyl acetate and the ethyl acetate extracts were combined. The combined extracts were washed with water, with saturated aqueous sodium chloride, and were then dried. Concentration in vacuo provided a reddish oil comprising ethyl 2-dimethylaminomethyl-5-methyl-4-thiazolecarboxylate. Yield = 21.2 g. (57%)

Two hundred milliliters of a one molar solution of lithium triethylborohydride in THF were cooled in an ice bath under a nitrogen atmosphere. A solution of 21.2 g. of ethyl 2-dimethylaminomethyl-5-methyl-4-thiazolecarboxylate in 60 ml. of THF was added in dropwise fashion over about 1.5 hours. The reaction mixture was maintained for an additional hour at 0° C. after which time it was decomposed by the cautious addition of 4 ml. of water plus 6 ml. of THF followed by 50 ml. of 6N aqueous hydrochloric acid. The resulting reaction mixture was concentrated in vauco and the residue treated with water. Solid potassium carbonate was added to the aqueous mixture to pH = 11. The resulting aqueous alkaline mixture was extracted several times with equal volumes of ethyl acetate. The ethyl acetate extracts were separated and combined and the combined extracts dried. The ethyl acetate was removed therefrom in vacuo to leave, as a residue, 2-dimethylaminomethyl-5-methyl-4-thiazole methanol; yield = 6.44 g. (44%).

Following the procedure of Example 3, a reaction mixture consisting of 6.4 g. of ethyl 2-dimethylaminomethyl-5-methyl-4-thiazolemethanol, 4.2 g. of cysteamine hydrochloride and 30 ml. of 48% aqueous hydrobromic acid was maintained at a temperature of about 100° C. under a nitrogen atmosphere for about 4 hours. The reaction mixture was cooled and the volatile constituents removed in vacuo. The resulting dark residue was twice trituated with ethanol and the ethanol removed by evaporation to remove residual HBr. The residue was then treated with 50 ml. of 5N aqueous sodium hydroxide. The alkaline layer was continuously extracted with ether over an 18 hour period. The ether extract was dried and the ether removed therefrom in vacuo to provide 2-(2-dimethylaminomethyl-5-methyl-4-thiazolylmethylthio)ethylamine prepared in the above reaction; yield = 1.38 g. The compound was a brown oil having the following physical characteristics:

The nmr spectrum in CDCl$_3$ (TMS internal standard) shows the following peaks ($\delta$): 1.48 (singlet, 2H), 2.35 (singlet, 6H), 2.42 (singlet, 3H), 2.80 (multiplets, 4H), 3.72 (singlet, 2H), 3.80 (singlet, 2H)

Following the procedure of Example 5, a stirred solution of 1.38 g. of 2-(2-dimethylaminomethyl-5-methyl-4-thiazolylmethylthio)ethylamine in 10 ml. of methanol was treated with N-methyl-1-methylthio-2-nitroethyleneamine. The reaction mixture was kept at room temperature overnight by which time all solids had dissolved. Thin layer chromatography (silica-10:10:1 ethyl acetate-methanol-ammonium hydroxide) indicated substantially a single product. The reaction mixture was concentrated by evaporation of the me±.-hanol and the resulting gummy yellow residue was triturated with several portions of cold ether, thus providing an off-white gum. Repeated trituration with cold 1,2-dimethoxyethane yielded N-2-(2-dimethylaminomethyl-5-methyl-4-thiazolylmethylthio)ethyl-N'-methyl-2-nitro-1,1-ethenediamine formed in the above reaction melting at about 104°–106° C.

Analysis Calculated: C, 45.19; H, 6.71; N, 20.27. Found: C, 45.54; H, 6.47; N, 19.60.

The compound had the following physical characteristics:

The nmr spectrum in CDCl$_3$ (TMS internal standard) shows the following peaks ($\delta$): 2.33 (singlet, 6H), 2.40 (singlet, 3H), 2.85 (multiplet, 2H), 2.97 (doublet, 3H), 3.48 (multiplet, 2H), 3.68 (singlet, 2H), 3.82 (singlet, 2H), 6.67 (singlet, 1H), 10.3 (broad, less than 2H).

EXAMPLE 10

Preparation of N-4-(2-dimethylaminomethyl-4-thiazolyl)butyl-N'-methyl 2-nitro-1,1-ethenediamine Following the procedure of Example 1, a stirred solution containing 3.2 g. of dimethylamirothioacetamide hydrochloride, and 6.48 g of bromomethyl 4-phthalimidobutyl ketone [prepared by the procedrre of *Chem. Listy.*, 49, 1385 (1955); *C.A.*, 50, 5573c (1956)]; in 50 ml. of ethanol was heated at refluxing temperature for about 5 hours and was then cooled. Volatile constituents were removed by evaporation in vacuo leaving 2-dimethylaminomethyl-4-(4-phthalimido-1-butyl)-thiazole as a semi-solid residue. The compound was utilized without further purification.

A solution was prepared containing the above product in 50 ml. of methanol. While the solution was being stirred, 2 ml. of 85% hydrazine hydrate were added and the resulting mixture heated to refluxing temperature for about 2 hours. At this point, an additional 2 ml. of 85% hydrazine hydrate were added and the heating continued for an additional two hours. The reaction mixture was then diluted with 4 volumes of water and the aqueous mixture made strongly basic with concentrated aqueous sodium hydroxide. The resulting alkaline layer was extracted continuously with ether for a 24 hour period. The ether extract was dried and the ether removed therefrom in vacuo to provide 4-(2-dimethylaminomethyl-4-thiazolyl)butylamine as a brown oil; weight=1.81 g. (42% yield from bromoketone). Mass spectrum: m/e at 152, 138, 128, 112, 96, 79, 71, 58, 42, 30 and 15.

A solution of 1.1 g. of the primary amine produced in the preceding step in 15 ml. of methanol was stirred while a solution of 3.20 g. of N-methyl 1-methylthio-2-nitroethyleneamine in methanolic solution was added thereto. The reaction mixture was maintained at room temperature for about 24 hours during which time evolution of methylmercaptan was noted. The progress of the reaction was followed by tlc. After the reaction had gone to completion according to tlc analysis, the volatile constituents were removed -in vacuo and the resulting residue dissolved in a 9:1 ethyl acetate-methanol solvent mixture. This solution was placed on 15 g. of Woelm silica and the chromatogram developed with the same solvent mixture. Fractiors shown by tlc to contain N-4-(2-dimethylaminomethyl-4-thiazolyl)butyl-N'-methyl 2-nitro-1,1-ethenediamine formed in the above reaction were combined and the solvent evaporated from the combined fractions in vacuo leaving a residual gum. Repeated trituration of this gum with small volumes of toluene followed by repeated recrystallization of the triturated solid from benzene provided off-white crystals melting at 97°-99° C.

Analysis Calculated: C, 49.82; H, 7.40; N, 22.35; S, 10.23.
Found: C, 49.56; H, 7.25; N, 22.12; S, 9.95.

The compound had the following peaks by mass spectral analysis: m/e at 236, 212, 194, 178, 153, 126, 112, 97, 85, 71, 58, 42, 32 and 15.

EXAMPLE 11

Preparation of N-methyl-N'-2-[2-(4-morpholinomethyl)-4-thiazolylmethylthio]ethyl 2-nitro-1,1-ethenediamine.

Following the procedure of Example 1, 4-morpholinothioacetamide hydrochloride was condensed with ethyl bromopyruvate to yield ethyl 2-(4-morpholinomethyl)-4-thiazolecarboxylate, melting at 129°-130° C. after recrystallization from a methylene dichlorideethyl acetate solvent mixture.

Analysis Calculated: C, 51.54; H, 6.29; N, 10.93.
Found: C, 51.36; H, 6.05; N, 10.88.

Following the procedure of Example 2, the above ester was reduced to the corresponding thiazolemethanol, 2-(4-morpholinomethyl)-4-thiazolemethanol, having an nmr spectrum in CDCl$_3$ (TMS internal standard) showing the following signals ($\delta$) : 2.55 (multiplet, 4H), 3.35–3.90 (singlet plus multiplet, 6H), 4.70 (3H), 7.13 (singlet, 1H).

Reaction of the thiazolemethanol with cysteamine hydrochloride by the procedure of Example 3 yielded 2-[2-(4-morpholinomethyl)-4-thiazolylmethyl-thio]ethylamine having the following physical characteristics:

nmr spectrum in CDCl$_3$ (TMS internal standard) showing the following signals ($\delta$): 1.83 (singlet, 2H), 2.3–3.1 (multiplet, 8H), 3.4–3.9 (multiplet plus singlets, 8H), 7.03 (singlet, 1H).

Following the procedure of Example 5, the 2-[2-(4-morpholinomethyl)-4-thiazolylmethylthio]ethylamine was reacted with N-methyl-1-methylthio-2-nitroethyleneamine to yield N-methyl-N'-2-[2-(4-morpholinomethyl)-4-thiazolylmethylthio]ethyl-2-nitro-1,1-ethenediamine melting at 151°-153° C. after recrystallization from a methanol-ethyl acetate solvent mixture.

Analysis Calculated: C, 45.02; H, 6.21; N, 18.75.
Found: C, 45.23; H, 6.24; N, 18.56.

EXAMPLE 12

Preparation of N-methyl-N'-2-[2-(1-pyrrolidinomethyl)-4-thiazolylmethylthio]ethyl 2-nitro-1,1-ethenediamine.

The same sequence of reactions as in Example 11 were carried out starting with 1-pyrrolidinomethylthioacetamide hydrochloride to yield the following intermediates.

Ethyl 2-(1-pyrrolidino)-4-thiazolecarboxylate. M.P. =81°-81.5° C. after recrystallization from a toluene-ethyl acetate solvent mixture.

nmr spectrum in CDCl$_3$ (TMS internal standard) showed the following signals ($\delta$): 1.40 (triplet 3H). 1.82 (multiplet, 4H), 2.70 (multiplet, 4H), 4.02 (singlet, 2H), 4.45 (quartet, 2H), 8.17 (singlet, 1H).

2-(1-pyrrolidinomethyl)-4-thiazolemethanol. nmr spectrum in CDCl$_3$ (TMS internal standard) gave the following signals ($\delta$): 1.77 (multiplet, 4H), 2.65 (multiplet, 4H), 3.92 (singlet, 2H), 4.73 (singlet, 3H), 7.15 (singlet, 1H).

2-[2-(1-pyrrolidinomethyl)-4-thiazolyl]-methylthio]ethylamine trihydrobromide was crystallized from isopropanol.

The ethylamine obtained from the above hydrobromide was reacted with N-methyl-1-methylthio-2-nitroethyleneamine to yield N-methyl-N'-2-[2-(1-pyrrolidinomethyl)-4-thiazolylmethylthio]ethyl 2-nitro-1,1-ethenediamine melting at 119°-120° C. after recrystallization from a methanol-ethyl acetate solvent mixture.

Analysis calculated: C, 47.04; H, 6.49; N, 19.59.
Found: C, 46.81; H, 6.55; N, 19.04.

EXAMPLE 13

Preparation of N-methyl-N'-2-[2-(1-piperidinomethyl)-4-thiazolylmethylthio]ethyl 2-nitro-1,1-ethenediamine.

Following the sequence of reactions of Example 11, the following intermediates were produced from 1-piperidinothioacetamide hydrochloride.

Ethyl 2-(1-piperidinomethyl-4-thiazolecarbosylate melting at 95°-97° C.

nmr in CDCl$_3$ (TMS internal standard) gave the following signals ($\delta$): 1.40 (triplet, 3H), 1.53 (multiplet, 6H), 2.53 (multiplet, 4H), 3.85 (singlet, 2H), 4.45 (quartet, 2H), 8.20 (singlet, 1H).

2-(1-piperidinomethyl)-4-thiazolemethanol having an nmr spectrum in CDCl$_3$ (TMS internal standard) which gave the following signals (δ): 1.53 (multiplet, 6H), 2.47 (multiplet, 4H), 3.77 (singlet, 2H), 4.77 (singlet, >3H), 7.13 (singlet, 1H).

2-[2-(1-piperidinomethyl)-4-thiazolylmethylthio]ethylamine trihydrobromide crystallized from isopropanol. The nmr spectrum in DMSOd$_6$ (TMS internal standard) showed the following signals (δ): 1.77 (multiplet, 6H), 2.6–3.8 (8H, multiplets), 3.97 (singlet, 2H), 4.80 (singlet, 2H), 7.80 (singlet, 1H), 8.12 (broad, 3H).

The primary amine obtained from the above salt was reacted with N-methyl 1-methylthio-2-nitro-ethyleneamine to yield N-methyl-N'-2-[2-(1-piperidinomethyl)-4-thiazolylmethylthio]ethyl 2-nitro-1,1-ethenediamine melting at about 100°–103° C. after recrystallization from a methanol-ethyl acetate solvent mixture.

Analysis calculated: C, 48.49; H, 6.78; N, 18.85.
Found: C, 48.72; H, 6.94; N, 18.64.

EXAMPLE 14

Preparation of N-methyl-N'-2-[2-(methylethylaminomethyl)-4-thiazolylmethylthio]ethyl 2-nitro-1,1-ethenediamine.

Following the reaction sequence of Example 11 starting with the reaction of N-methyl-N-ethyl aminothioacetamide hydrochloride and ethyl bromopyruvate, the following intermediates were prepared:

Ethyl 2-(methylethylaminomethyl)-4-thiazolecarboxylate, a non-crystallizable oil.

2-(methylethylaminomethyl)-4-thiazolemethanol having an nmr spectrum in CDCl$_3$ (TMS internal standard) showing the following signals (δ): 1.10 (triplet, 3H), 2.33 (singlet, 3H), 2.53 (quartet, 2H), 3.80 (singlet, 2H), 4.73 (singlet, 2H), 5.30 (singlet, 1H), 7.20 (singlet, 1H).

2-[2-(methylethylaminomethyl)-4-thiazolylmethylthio]ethylamine having an nmr spectrum in CDCl$_3$ (TMS internal standard) showing the following signals (δ): 1.08 (triplet, 3H), 1.57 (singlet, 2H), 2.33 (singlet, 3H), 2.2–3.0 (multiplets, 6H), 3.78 (apparent singlet, 4H), 7.03 (singlet, 1H).

The above primary amine was reacted with N-methyl 1-methylthio-2-nitroethyleneamine to yield N-methyl-N'-2-[2-methylethylaminomethyl)-4-thiazolylmethylthio]ethyl 2-nitro-1,1-ethenediamine melting at 114°–116° C. after recrystallization from a methanolethyl acetate solvent mixture.

Analysis calculated C, 45.19; H, 6.71; N, 20.27.
Found: C, 45.48 H, 6.80; N, 19.98.

EXAMPLE 15

Preparation of N-methyl-N'-2-(2-dimethylaminomethyl-4-thiazolylmethylthio)ethyl-N''-aminocarbonylguanidine.

About 0.6 g. of N-methyl-N'-2-(2-dimethylaminomethyl-4-thiazolylmethylthio)ethyl-N''-cyanoguanidine were dissolved in 8 ml. of 1.5N aqueous hydrochloric acid. The resulting solution was allowed to remain at ambient temperature for about four days. Volatile constituents were then removed by evaporation in vacuo. The resulting residue, comprising N-methyl-N'-2-(2-dimethylaminomethyl-4-thiazolylmethylthio)ethyl-N''-aminocarbonylguanidine dihydrochloride formed in the above reaction, was dissolved in ethanol and the ethanol removed by evaporation. The residue obtained thereby was recrystallized from isopropanol. The crystalline product was collected and digested with ethyl acetate. The ethyl acetate was removed by evaporation and the product obtained was crystallized from isopropanol to yield N-methyl-N'-2-(2-dimathylaminomethyl-4-thiazolylmethylthio)ethyl-N'-aminocarbonylguanidine dihydrochloride melting at 156.5°–159.5° C.

Analysis Calculated for $C_{12}H_{23}Cl_2N_6OS_2$:
C, 35.82; H, 5.76; Cl, 17.62; O, 3.98.
Found: C, 35.64; H, 6.30; Cl, 17.73; O, 4.38.

EXAMPLE 16

Preparation of N-2-(2-dimethylaminomethyl-4-thiazolylmethylthio)ethyl-N'-cyclopropyl 2-nitro-1,1-ethenediamine.

A reaction mixture was prepared containing 2.31 g of 2-(2-dimethylaminomethyl-4-thiazolylmethylthio)ethylamine, and 1.65 g of 1-nitro-2,2-bis(methylthio)ethylene in 30 ml. of acetonitrile. The reaction mixture was heated to reflux temperature for about four hours after which time the solvent was removed by evaporation. The resulting residue was chromatographed over silica using ethyl acetate as the eluant. Fractions shown by tlc to contain the desired product were combined and the solvent evaporated therefrom to yield 1-[2-(2-dimethylaminomethyl-4-thiazolylmethylthio)ethyl]-amino)-1-methylthio-2-nitroethylene (2.39 g.) Melting at about 68.5°–70.0° C. after recrystallization from ethyl acetate.

Analysis: Calculated: C, 41.36; H, 5.78; N, 16.08; S, 27.60.
Found: C, 41.54; H, 5.61; N, 16.14; S, 27.54.

A reaction mixture, prepared from 1-[2-(2-dimethylaminomethyl-4-thiazolylmethylthio)ethyl]amino-1-methylthio-2-nitroethylene, cyclopropylamine and ethanol, was heated to refluxing temperature for about three hours. The solvent was then removed by evaporation and the resulting residue was chromatographed over silica using a gradient elution technique. The desired compound was eluted with a 5:95 methanol:ethyl acetate solvent mixture. Removal of the solvent yielded N-2-(2-dimethylaminomethyl-4-thiazolylmethylthio)ethyl-N'-cyclopropyl 2-nitro-1,1-ethenediamine which melted at 128.5°–131.5° C. after recrystallization from a methanol/ethyl acetate solvent mixture.

Analysis: Calculated: C, 47.04; H, 6.49; N, 19.59.
Found: C, 47.31; H, 6.12; N, 19.35.

Following the above procedure using 2-hydroxyethylamine there was obtained N-2-(2-dimethylaminomethyl-4-thiazolylmethylthio)ethyl-N'-(2-hydroxy)ethyl 2-nitro-1,1-ethenediamine obtained as a glass which was eluted from a silica chromatographic column with a 94:5:1 ethyl acetate:methanol:ammonium hydroxide (0.88 sp. gr.) solvent mixture as the eluant. $R_f=0.43$ on silica using a 95:5 ethanol:ammonium hydroxide solvent mixture.

nmr (CDCl$_3$): δ at 2.37 (s, 6H); 2.80 (trip, 2H); 3.1–3.6 (multiplets, 4H); 3.74 (s, 2H); 3.85 (s, 1H); ca. 3.8 (multiplet unresolved, 2H); 6.58 (s, 1H); 7.11 (s, 1H); 7.80 (br, 1H); 10.36 (br, 1H).

EXAMPLE 17

Preparation of
N-3-(2-dimethylaminomethyl-4-thiazolylmethylthio)-propyl-N'-methyl 2-nitro-1,1-ethenediamine Following the procedure of Example 3, 10 g of 2-dimethylaminomethyl-4-thiazolylmethanol, 9.2 g of homocysteamine (3-aminopropanethiol) hydrobromide and 100 ml of 48% aqueous hydrobromic acid were heated to reflux temperature for about six hours. Volatile constituents were removed by evaporation and the crystalline residue was triturated with isopropanol. The isopropanol was decanted. This procedure was repeated several times. The crystalline product was finally filtered to yield 7.0 g of 3-(2-dimethylaminomethyl-4-thiazolylmethylthio)propylamine trihydrobromide melting at 179°–181° C. (hygroscopic).

Analysis: Calculated: C, 24.61; H, 4.54; Br, 49.11; N, 8.61.
Found: C, 24.46; H, 4.34; Br, 49.31; N, 8.38.

A reaction mixture was prepared from .8 g of the above thiazolylmethylthiopropylamine and 0.53 g of 1-methylamino-1-methylthio-2-nitroethylene in 10 ml of ethanol. The reaction mixture was heated to reflux temperature for about 20 hours after which time the solvent was removed by evaporation and the resulting residue triturated with ether. N-3-(2-dimethylaminomethyl-4-thiazolylmethylthio)propyl-N'-methyl 2-nitro-1,1-ethenediamine thus prepared had the following physical characteristics:

Analysis Calculated: C, 45.19; H, 6.71; N, 20.27;
Found: C, 45.25; H, 6.51; N, 19.99.
nmr (CDCl$_3$): δ at 1.93 (quintet, 2H); 2.42 (s, 6H); 2.65 (trip, 2H); 2.92 (br, 3H); 3.34 (multiplet, 2H); 3.81 (s, 2H); 3.83 (s, 2H); 6.58 (s, 1H); 7.10 (s, 1H).

EXAMPLE 18

Preparation of
3-[2-(2-dimethylaminomethyl-4-thiazolylmethylthio)ethyl]amino-4-methylamino-3-cyclobutene-1,2-dione A solution was prepared from 568 mg of 3,4-dimethoxy-3-cyclobutene-1,2-dione and 15 ml of methanol. A second solution containing 925 mg of 2-[2-(dimethylaminomethyl)-4-thiazolylmethylthio]ethylamine in 25 ml of methanol was added to the first solution with stirring over a period of about 1.5 hours. After three hours a small amount of solid was removed from the reaction mixture by filtration. The filtrate was evaporated to a volume of about 10 ml and 6 ml of a 35% solution of methylamine in ethanol was added thereto. After a reaction time of about 2.25 hours, a solid had separated. This solid was filtered and the filter cake washed with methanol. Recrystallization of the filter cake from ethanol gave 0.72 g of 3-[2-(2-dimethylaminomethyl-4-thiazolylmethylthio)ethyl]amino-4-methylamino-3-cyclobutene-1,2-dione melting at 163°–167° C.

Analysis: Calculated: C, 49.39; H, 5.92; N, 16.46; O, 9.40.
Found: C, 49.49; H, 6.01; N, 16.18; O, 9.59.

EXAMPLE 19

Alternate preparation of
N-methyl-N'-2-(2-dimethylaminomethyl-4-thiazolylmethylthio)ethyl-N"-cyanogunidine About 0.6 g of sodium were added to 50 ml. of dry ethanol under an N$_2$ atmosphere, thus forming sodium ethylate in ethanol. 0.91 g of N-methyl-N'-(2-mercapto)-ethyl-N"-cyanoguanidine (prepared by the procedure of U.S. Pat. No. 4,093,621) dissolved in 10 ml. of anhydrous ethanol was added thereto and the resulting mixture stirred at room temperature for about 1 hour. Next, 1.59 g of 2-dimethylaminomethyl-4-thiazolylmethylchloride hydrochloride was added thereto in portions over a 1 hour period. After the addition had been completed, the reaction mixture was stirred for an hour at room temperature and was then heated to refluxing temperature for an additional hour. The ethanol was removed from the reaction mixture by evaporation and ethyl acetate plus water (10:1) were added to the residue. The pH of the aqueous phase was adjusted to pH=8 with 1N aqueous hydrochloric acid. The ethyl acetate extract was separated and the ethyl acetate removed by evaporation. The residue was subjected to high pressure liquid chromatography (silica-20:80 ethanol/ethyl acetate). Fractions containing the desired product as shown by tlc were combined and the solvent evaporated therefrom. 1.10 g of N-methyl-N'-2-(2-dimethylaminomethyl-4-thiazolylmethylthio)ethyl-N"-cyanoguanidine were obtained. The physical properties were substantially identical with those obtained in Example 4 for the same compound.

Analysis: Calculated: C, 46.13; H, 6.45; N, 26.90.
Found: C, 46.04; H, 6.58; N, 26.63.

In flow chart A above, compound I is a substituted aminothioacetanide hydrohalide of the structure $$R^1\!\!\underset{R^2}{\diagup}\!\!N-CH_2-\overset{S}{\overset{\|}{C}}-NH_2 \cdot HX$$

Where the substituting groups are alkyl, the compounds are known as, for example, dimethylaminothioacetamide, diethylaminothioacetamide, etc. and can be prepared by the method of *J. Org. Chem.*, (Russia), 6, 884 (1970) in English.

Illustrated preparations are given below.

PREPARATION 1

Morpholinothioacetamide

A reaction mixture was prepared from 203 ml. each of triethylamine and pyridine plus 63 g. of morpholinoacetonitrile. Hydrogen sulfide was bubbled through the heated, stirred reaction mixture for about 2.5 hours. Stirring was continued overnight at ambient temperature. The next day, H$_2$S was passed through the heated, stirred reaction mixture for an additional 1.5 hours. At this point, the solvents were evaporated in vacuo and the residue triturated with ether. The ether was discarded and the residue dissolved in ethanol. Crystalline morpholinothioacetamide precipitated and was separated by filtration. Treatment of the filtrate with alcoholic hydrogen chloride yielded morpholinothioacetamide hydrochloride melting in the range 64°–80° C. See also *J.A.C.S.*, 72, 2804 (1950).

Following the above procedure but using piperidinoacetonitrile in place of morpholinoacetonitrile, there was prepared piperidinothioacetamide hydrochloride melting at 166°-168° C., after recrystallization from ethylacetate. See also *Helv. Chim. Act.*, 43, 659 (1960).

Yield 35 g. from 62 g. of piperidinoacetonitrile starting material.

Following the above procedure using 100 g. of pyrrolidinoacetonitrile, there were obtained 68.4 g. of pyrrolidinothioacetamide hydrochloride (new) melting at about 195°-197° C.

Analysis Calculated: C, 39.88; H, 7.25; N, 15.50 S, 17.74.
Found: C, 39.66; H, 6.99; N, 15.76; S, 17.84.

Following the above procedure but using 49 g of methylethylaminoacetonitrile, 200 ml of triethylamine and 200 ml of benzene, there was prepared N-methyl-N-ethylaminothioacetamide hydrochloride (new) melting at 115°-117° C.

The compounds of formula (XX) in which B is NHR are potent $H_2$-receptor antagonists and are useful in a method of inhibiting $H_2$ histamine receptors. They are also anti-ulcer agents useful in a method of inhibiting gastric acid secretion in mammals. The relation of the $H_2$-receptors to mammalian gastric secrection is described in an article by Black et al. *Nature*, 236, 385 (1972).

The following assay for $H_2$-receptor blocking activity was employed. Female albino rats were treated with estrone 24 hours prior to the initiation of the experiment. The rats were sacrificed and the uterine horns removed therefrom and suspended at ambient temperatures in isolated organ baths containing De Jalon's solution. After equilibration, the uterine strips are exposed to 50 millimole aqueous potassium chloride, which produces a sustained contraction. When the uterus is so contracted, histamine produces a dose-dependent $H_2$-receptor-mediated relaxation. A control dose-response curve to histamine is constructed on each tissue. Following thorough washout of the histamine after obtaining the control dose-response curve, each antagonist (the compounds of this invention) is added for 30 minutes at a concentration of $10^{-5}$ molar. The uterine strips are then contracted with aqueous potassium chloride in the presence of the antagonist and a second dose-response curve to histamine obtained. In the presence of a competitive antagonist, the dose-response curve to histamine is shifted in parallel to the right with no depression of the maximum relative to the control curve. The dose ratio (DR) is calculated for each concentration of antagonist by dividing the $ED_{50}$ of histamine in the presence of the competitive antagonist by the control $ED_{50}$ for histamine. The dissociation constant ($K_B$) of the antagonist is calculated from the dose-ratios by the following equation:

$$K_B = [\text{antagonist}]/(DR - 1)$$

and the $-\log K_B$ values are claculated therefrom. Cimetidine and Ranitidine are included as internal standards.

Results of the above assay carried out on representative compounds of this invention are set forth in Table 1 below. In the table, columns 1-4 list the substituents at various places in the general formula at the head of the Table and column 5 the $-\log K_B$ values.

TABLE 1

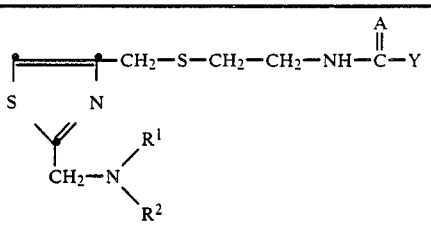

| Y | $R^1$ | $R^2$ | A | $-\log K_B$ |
|---|---|---|---|---|
| $NHCH_3$ | $CH_3$ | $CH_3$ | $CHNO_2$ | 7.02 |
| $NHC_2H_5$ | $CH_3$ | $CH_3$ | $CHNO_2$ | 6.98 |
| NHcyclopropyl | $CH_3$ | $CH_3$ | $CHNO_2$ | 6.86 |
| $NHC_2H_4OH$ | $CH_3$ | $CH_3$ | $CHNO_2$ | 6.83 |
| $SCH_3$ | $CH_3$ | $CH_3$ | $CHNO_2$ | 6.18 |
| $NHCH_3$ | $CH_3$ | $C_2H_5$ | $CHNO_2$ | 6.93 |
| $NHCH_3$ | pyrrolidinyl | | $CHNO_2$ | 5.91 |
| $NHCH_3$ | piperidinyl | | $CHNO_2$ | 6.20 |
| $NHCH_3$ | morpholinyl | | $CHNO_2$ | 5.59 |
| $NHCH_3$ | $CH_3$ | H | $CHNO_2$ | 5.92 |
| $NHCH_3$ | $CH_3$ | $CH_3$ | NCN | 6.44 |
| $NHC_2H_5$ | $CH_3$ | $CH_3$ | NCN | 6.22 |
| $SCH_3$ | $CH_3$ | $CH_3$ | NCN | 6.49 |
| $NHCH_3$ | $CH_3$ | $CH_3$ | $N-CONH_2$ | 6.05 |
| $NHCH_3$ | $CH_3$ | $CH_3$ | $N-SO_2CH_3$ | 6.19 |
| $NHCH_3$ | $CH_3$ | $CH_3$ | $N-SO_2-p$-tolyl | 6.68 |
| $NHCH_3$ | $CH_3$ | $CH_3$ | $N-NO_2$ | 6.97 |
| $NHCH_3$ | $CH_3$ | $CH_3$ | S | 6.76 |
| cimetidine | | | | 6.17 |
| ranitidine | | | | 6.61 |

In addition to the compounds in Table 1, the assay was also run on N-4-(2-dimethylaminomethyl-4-thiazolyl)butyl-N'-methyl-2-nitro-1,1-ethenediamine (the compound of Example 10) and 3-[2-(2-dimethylaminomethyl-4-thiazolylmethylthio)ethyl]amino-4-methylamino-3-cyclobutene-1,2-dione (the compound of Example 18). The $-\log K_B$ value found for the compounds was 6.47 and 6.38, respectively.

A second assay for $H_2$-receptor blocking activity employs the isolated bullfrog gastric mucosa—see Warrick and Lin, *Communications in Chem. Pathology and Pharmacology*, 13, 149 (1976). The assay is carried out as follows: The gastric mucosa of the bullfrog (*Rana catesbeiana*) is separated from the musculature of the stomach and placed between a pair of Using chambers made of lucite. The chambers are filled with frog Ringer solution and acid secretion is stimulated by addition of histamine to the serosal side of the mucosa at a final concentration of $10^{-5}M/1$. Acid output is automatically titrated to pH 4.5. After steady response to $10^{-5}M/1$ of histamine is established, the antagonist (a compound of this invention) is added to the serosal chamber and the maximal inhibition by each concentration of the $H_2$-antagonist is recorded. From the dose-response curve, the $ED_{50}$ of the drug is calculated. The relative potency of each unknown antagonist is calculated by dividing the $ED_{50}$ for cimetidine by the $ED_{50}$ of the drug in question. N-methyl-N'-2-(2-dimethylaminomethyl-4-thiazolylmethylthio)ethyl 2-nitro-1,1-ethenediamine had a relative potency of 17.78 compared to 1.0 for cimetidine.

An in vivo assay for antisecretory action of drugs on acid secretion utilizes gastric fistula dogs with vagally innervated gastric fistula and vagally denervated Heidenhain pouch. In this procedure, a steady-state gastric secretion is produced by the iv infusion of histamine. The antisecretory drugs under test are given either intravenously by infusion over a 30 minute period or orally 75 min. prior to collection of gastric secretion from the fistula. N-methyl-N'-2-(2-dimethylaminomethyl-4-thiazolylmethylthio)ethyl 2-nitro-1,1-ethenediamine was about 6.5 times as active as cimetidine by the intravenous route and about 11.0 times as active orally using this procedure.

These last results indicate that N-methyl-N'-2-(2-dimethylaminomethyl-4-thiazolylmethylthio)-ethyl 2-nitro-1,1-ethenediamine and other compounds of this invention are better absorbed orally than cimetidine or other recently developed histamine $H_2$-antagonists. This greater oral absorption is also indicated by a relatively greater oral toxicity (compared to iv toxicity) for the compounds of this invention. $LD_{50}$'s have been determined for the above ethenediamine and for cimetidine as follows: For N-methyl-N'-2-(2-dimethylaminomethyl-4-thiazolylmethylthio)ethyl 2-nitro-1,1-ethenediamine, the following $LD_{50}$'s were obtained: mouse iv 265 mg/kg, mouse oral 1685 mg/kg; rat iv above 300 mg/kg, rat oral 1680 mg/kg. Literature $LD_{50}$'s for cimetidine are 150, 2600, 106 and 5000 mg/kg respectively. The relative lack (relative to cimetidine) of toxicity by the intravenous route of the compounds of this invention is surprising as is the greater oral absorption.

The above figures as to potency and toxicity indicate a favorable therapeutic ratio for the compounds of this invention. It appears that certain of the compounds of this invention have a longer duration of action than cimetidine when equimolar amounts are administered. When equipotent amounts are given there is no apparent difference in duration of action.

In utilizing the compounds of this invention as antisecretory agents, either the parenteral or oral route of administration may be employed.

In one embodiment of the invention, there is provided a pharmaceutical formulation which comprises as an active ingredient, a compound of formula XX in which B is NHR, or a pharmaceutically-acceptable salt thereof, associated with one or more pharmaceutically-acceptable carriers therefor. Orally-acceptable formulations such as capsules or tablets constitute the preferred mode of administration.

For oral dosage, a suitable quantity of a free base of this invention, or a pharmaceutically-acceptable salt thereof, is mixed with one or more conventional excipients such as starch and the mixture placed in telescoping gelatin capsules or compressed into tablets each typically containing from 100–400 mg. of active ingredients. The tablets may be scored if lower or divided dosages are to be used. For parenteral administration via an iv infusion, an isotonic solution of a salt is preferably employed although a soluble free base is also useful in isotonic preparations.

Because of the higher oral absorption and longer duration of action of the compounds of this invention, particularly N-methyl-N'-2-(2-dimethylaminomethyl-4-thiazolylmethylthio)ethyl 2-nitro-1,1-ethenediamine, it is believed that oral administration of about 50–80 mg. three times a day or 100–200 mg. twice a day will suffice to control acid secretion in ulcer patients and thus alleviate ulcer symptoms. Generally, however, the compounds of this invention are administered to humans orally in a daily dosage range of 140–800 mg. Smaller dosages at more frequent intervals may also be employed. The preferred oral dosage range is about 2–5 mg./kg./day of mammalian body weight, although a dosage of from 1–10 mg./kg./day can be used.

I claim:
1. A compound of the formula

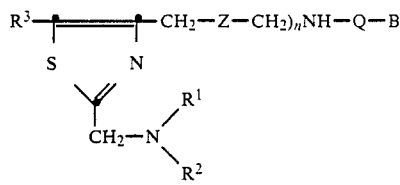

wherein
$R^1$ represents hydrogen, methyl, ethyl, benzyl or benzoyl; $R^2$ represents methyl or ethyl; or $R^1$ and $R^2$ taken together with the nitrogen atom to which they are attached, form a piperidino, pyrrolidino or morpholino radical;
$R^3$ is hydrogen or methyl;
Z is O, S or $CH_2$;
n is 2 or 3 when Z is O or S and n is 1, 2 or 3 when Z is $CH_2$;
Q is

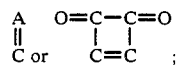

wherein A is N-CN, N-$NO_2$, CH-$NO_2$, S, N-$SO_2$-aryl, N-$SO_2$-methyl or N-CO-$NH_2$, wherein aryl is phenyl or tolyl; and
B is NHR, wherein R is methyl, ethyl, cyclopropyl or (2-hydroxy)ethyl; or
B is $YR^4$, wherein Y is oxygen or sulfur and $R^4$ is ($C_1$-$C_3$) alkyl, -$CH_2$-($C_2$-$C_4$) alkenyl or benzyl; provided that when Q is

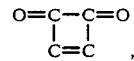

B is NHR or O—($C_1$–$C_2$)-alkyl; and acid addition salts thereof.
2. A thiazole derivative as claimed in claim 1 wherein $R^1$ is hydrogen, methyl, ethyl, benzyl or benzoyl; $R^2$ is methyl or ethyl; or $R^1$ and $R^2$ taken together with the adjacent nitrogen atom represent a piperidino, pyrrolidino or morpholino group; $R^3$ is hydrogen or methyl; A is N-CN, N—$NO_2$, CH-$NO_2$, S, N-$SO_2$-aryl, N-$SO_2$—methyl or N-CO-$NH_2$, where aryl is phenyl or tolyl; B is NHR or $YR_4$ wherein R is methyl, ethyl, cyclopropyl or 2-(hydroxy)ethyl and $R^4$ is ($C_1$-$C_3$)alkyl; provided that when B is $YR^4$, Q is C=A; or a pharmaceutically-acceptable, acid addition salt thereof.
3. A thiazole derivative as claimed in claim 1, wherein Z is sulfur.
4. A thiazole derivative as claimed in claim 1 wherein n is 2.
5. A thiazole derivative as claimed in claim 1, wherein $R^3$ is hydrogen.
6. A thiazole derivative as claimed in claim 1, wherein $R^1$ and $R^2$ are methyl.
7. A thiazole derivative as claimed in claim 1, wherein A is NCN or $CHNO_2$.
8. A thiazole derivative as claimed in claim 1, wherein B is NHR where R is methyl or ethyl.
9. A thiazole derivative as claimed in claim 8, wherein B is methylamino.

10. A compound according to claim 1 in which R³ is H, R¹ is H, methyl or ethyl, R² is methyl or ehtyl, Z is S, Q is

A is N-CN, N-NO₂ or CH-NO₂, B is NHR, and R is methyl or ethyl.

11. A compound according to claim 10, said compund being N-methyl-N'-2-(2-methylaminomethyl-4-thiazolylmethylthio)ethyl 2-nitro-1,1-ethenediamine.

12. A compound according to claim 10, said compound being N-methyl-N'-2-(2-dimethylaminomethyyl-4-thiazoIylmethylthio)ethyl-N"-cyanoguanidine.

13. A pharmaceutical formulation in unit dosage form adapted for oral administration to achieve an antisecretory effect, comprising per dosage unit an antisecretorially-effective amount of a compound of claim 1 wherein B is NHR plus one or more pharmaceutical excipients.

14. A pharmaceutical formulation in unit dosage form adapted for oral administration to achieve an antisecretory effect, comprising per dosage unit an antisecretorially-effective amount of a compound of claim 10 plus one or more pharm.aceutical excipients.

15. A pharmaceutical formulation according to claim 13 containing from 50-80 mg. of active drug per dosage unit.

16. A pharmaceutical formulation in unit dosage form adapted for oral administration to achieve an antisecretory effect, comprising per dosage unit an antisecretorially-effective amount of a compound according to claim 2 plus one or more pharmaceutical excipients.

17. A method for inhibiting gastric acid secretion in mammals which comprises administering to a mammal, whose gastric acid secretion is excessive and who is in need of treatment, an antisecretorially effective amount of a compound according to claim 1.

18. A method according to claim 17 in which from 140-350 mg. of drug per day are administered orally to humans.

19. A method according to claim 18 in which the oral daily dose is from 2-5 mg./kg. of mammalian body weight.

20. A method for inhibiting gastric acid secretion in mammals which comprises administering to a mammal, whose gastric acid secretion is excessive and who is in need of treatment, an antisecretorially effective amount of a compound according to claim 2.

21. A method for inhibiting gastric acid secretion in mammals which comprises administering to a mammal, whose gastric acid secretion is excessive and who is in need of treatment, an antisecretorially effective amount of a compound according to claim 10.

22. A method according to claim 17 in which the antisecretory drug is administerd orally.

23. A method according to claim 17 in which the antisecretory drug is administered parenterally.

24. A method of inhibiting H₂ histamine receptors which comprises administering to an animal an amount effective to inhibit said receptors of a compound according to claim 1 wherein B is NHR.

* * * * *

UNITED STATES PATENT AND TRADEMARK OFFICE
CERTIFICATE OF CORRECTION

PATENT NO. : 4,760,075

DATED : July 26, 1988

INVENTOR(S) : Richard P. Pioch

It is certified that error appears in the above—identified patent and that said Letters Patent is hereby corrected as shown below:

In column 5, line 30, change "$(C_1-OC_2)$" to -- $(C_1-C_2)$ --.

In column 6, line 15, change "4thiazolylmethylthio" to -- 4-thiazolylmethylthio --.

In column 26, line 42, and 43, change "me+.-hanol" to -- methanol --.

In column 26, line 67, change "procedrre" to -- procedure --.

In column 27, line 37, change "Fractiors" to -- Fractions --.

In column 30, line 7, change "N'-" to --N''- --.

In column 30, line 65, change "δat" to -- δ at --.

In column 32, line 5, change "-cyanogunidine" to -- cyanoguanidine --.

In column 34, line 45, change "Using" to -- Ussing --.

In column 35, line 28, change "cf" to -- of --.

In column 36, line 51, change "$YR_4$" to -- $YR^4$ --.

In column 37, line 14, change "dimethylaminomethyyl-" to -- dimethylaminomethyl --.

In column 37, line 15, change "4-thiazoIylmethylthio)" to -- 4-thiazolylmethylthio) --.

UNITED STATES PATENT AND TRADEMARK OFFICE
CERTIFICATE OF CORRECTION

PATENT NO. : 4,760,075
DATED : July 26, 1988
INVENTOR(S) : Richard P. Pioch

It is certified that error appears in the above—identified patent and that said Letters Patent is hereby corrected as shown below:

In column 37, line 26, change "pharm.aceutical" to -- pharmaceutical --.

In column 38, line 6, change "antisecretorially effective" to -- antisecretorially-effective --.

In column 38, line 25, change "administerd" to -- administered --.

Signed and Sealed this

Seventeenth Day of July, 1990

Attest:

HARRY F. MANBECK, JR.

Attesting Officer

Commissioner of Patents and Trademarks